(12) United States Patent
Hu et al.

(10) Patent No.: US 8,501,731 B2
(45) Date of Patent: Aug. 6, 2013

(54) DERIVATIVES OF 6[3-(TRIFLUOROMETHYL)PHENYL] PYRIDAZIN-3(2H)-ONE HAVING ANTITUMOR ACTIVITY

(75) Inventors: Youhong Hu, Shanghai (CN); Liguang Lou, Shanghai (CN); Shijun Lin, Shanghai (CN); Hongbing Zhao, Shanghai (CN); Zhende Liu, Shanghai (CN); Yongping Xu, Shanghai (CN); Bo Chao, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 165 days.

(21) Appl. No.: 12/933,104

(22) PCT Filed: Mar. 18, 2009

(86) PCT No.: PCT/CN2009/000295
§ 371 (c)(1),
(2), (4) Date: Nov. 17, 2010

(87) PCT Pub. No.: WO2009/114993
PCT Pub. Date: Sep. 24, 2009

(65) Prior Publication Data
US 2011/0112061 A1    May 12, 2011

(30) Foreign Application Priority Data

Mar. 18, 2008 (CN) .......................... 2008 1 0034796

(51) Int. Cl.
| | |
|---|---|
| *C07D 403/10* | (2006.01) |
| *C07D 401/10* | (2006.01) |
| *C07D 277/04* | (2006.01) |
| *C07D 237/04* | (2006.01) |
| *C07D 413/10* | (2006.01) |
| *A61K 31/55* | (2006.01) |
| *A61K 31/501* | (2006.01) |
| *A61P 35/00* | (2006.01) |

(52) U.S. Cl.
USPC ............ 514/217.05; 514/252.02; 514/252.03; 514/252.05; 514/248; 514/236.5; 540/598; 544/238; 544/239; 544/114

(58) Field of Classification Search
USPC .......... 540/598; 514/252.02, 252.01, 252.05, 514/217.04, 236.5, 252.03, 217.05, 248; 544/238, 224, 114, 239
See application file for complete search history.

(56) References Cited

U.S. PATENT DOCUMENTS

| | | | |
|---|---|---|---|
| 4,112,095 A | 9/1978 | Allen, Jr. et al. | |
| 4,117,030 A * | 9/1978 | Nelson .......................... | 525/531 |
| 5,462,914 A * | 10/1995 | Leitner et al. ................. | 504/238 |
| 2007/0072866 A1 | 3/2007 | Schoenafinger et al. | |
| 2007/0173503 A1 | 7/2007 | Hoelder et al. | |

FOREIGN PATENT DOCUMENTS

| | | |
|---|---|---|
| CN | 200380105057 | 11/2003 |
| EP | 0665223 A1 | 8/1995 |
| WO | 03/059891 A1 | 7/2003 |
| WO | 2004046130 A1 | 6/2004 |
| WO | 2005007632 A1 | 1/2005 |
| WO | 2005085231 A1 | 9/2005 |
| WO | 2005111019 A1 | 11/2005 |
| WO | 2006124874 A2 | 11/2006 |

OTHER PUBLICATIONS

Johnson, Am J Physiol Lung Cell Mol Physiol 296: L700-L709, 2009.*
Zhou, et al., Cancer Lett. Mar. 28, 2012;316(2):178-86.*
Mai, Clin Cancer Res 2009;15(22) Nov. 15, 2009 6810, 6810-6819.*
Kilian et al., Bronchospamolytic effects of substituted 6-phenyl-3[2H]-pyridazinoes in comparison to theophylline and enprofylline, Current Clinical Practice Series (1985), 19 (Anti-Asthma Xanthines adenosine) p. 209-213.

* cited by examiner

*Primary Examiner* — Susanna Moore
*Assistant Examiner* — Cecilia M Jaisle
(74) *Attorney, Agent, or Firm* — Kramer & Amado, P.C.

(57) ABSTRACT

The present invention relates to a class of pyridazinones of formula I, which comprises 6-[3-(trifluoromethyl)phenyl]pyridazin-3(2H)-one as a mother nucleus, the preparation method thereof and the use thereof in manufacturing medicaments against tumors, especially liver cancer.

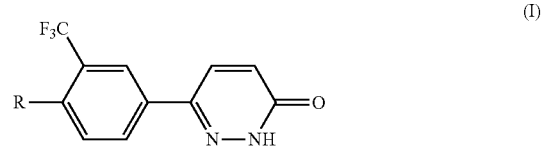

(I)

11 Claims, 1 Drawing Sheet

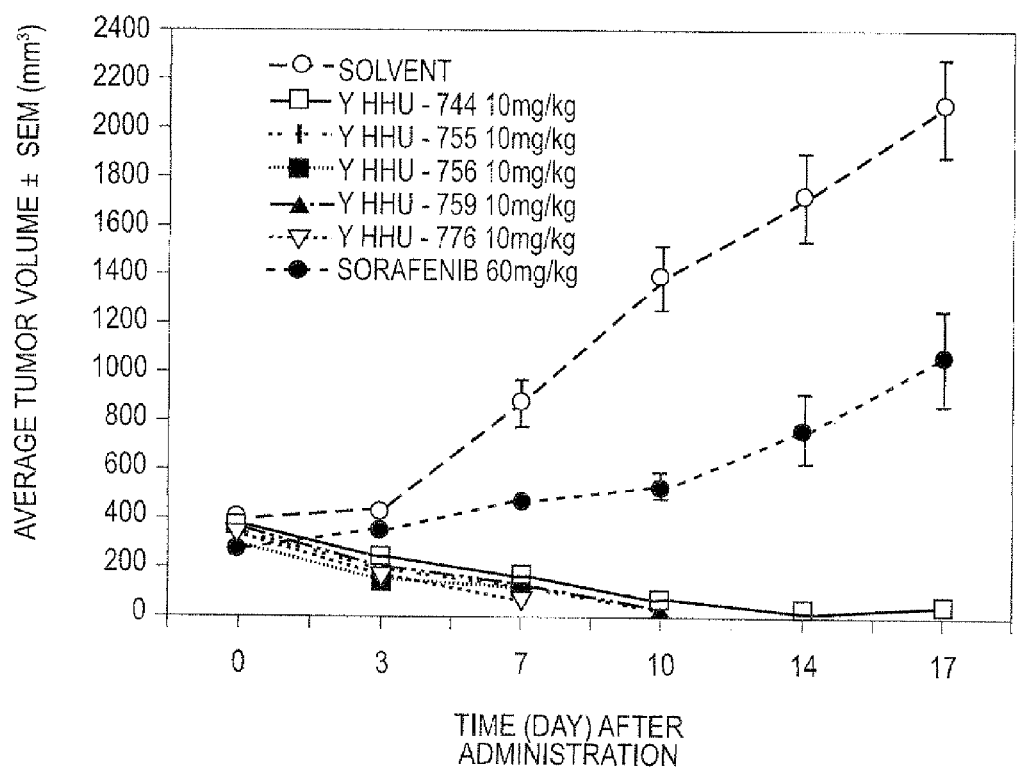

DERIVATIVES OF 6[3-(TRIFLUOROMETHYL)PHENYL]PYRIDAZIN-3(2H)-ONE HAVING ANTITUMOR ACTIVITY

TECHNICAL FIELD

The present invention belongs to the field of materia medica, and particularly relates to a series of novel pyridazinones containing the mother nucleus of 6-[3-(trifluoromethyl)phenyl]pyridazin-3(2H)-one, the preparation method and the use thereof. The above pyridazinones show significant antitumor activities, especially for liver cancer.

BACKGROUND OF THE INVENTION

Pyridazinones have shown a broad-spectrum biological activity, e.g. as an antidepressant, a vasodilatator, a cardiotonic, an acesodyne/anti-inflammatory agent or an antihypertensive, as acaricide or herbicide in agriculture, and also as inhibitors for acetylcholine esterase, aldose reductase, monoamine oxidase, CDKs, COX-2 and P38MAP kinase, etc. Some pyridazinones have exhibited an antitumor activity to a certain extent. US2007/0072866 A1 reported a series of pyridazinones having a structure formula of

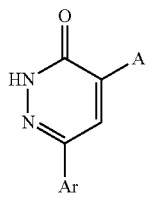

as a GSK-3β inhibitor, which can be used for treating metabolic diseases, neurodegenerative diseases or other related diseases or disorders. CN200380105057 further defines that A is C(O)NHR or NHC(O)R; while in US2007/0072866A1, A is defined as a heterocyclic substituent.

WO 03/059891 and WO 2005/007632 disclose that pyridazinones are useful for treating diseases or conditions caused or exacerbated by unregulated P38 MAP kinase and/or TNF activity. In the above patent literatures, the pyridazinones have a structure formula of

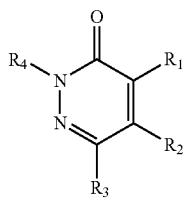

and are useful for treating inflammatory diseases, diabetes, Alzheimer's disease or cancer. Although the described pyridazinones covers almost all substituents, actually, $R_4$ is mainly aryl, $R_1$ is mainly halogen, $R_2$ is various kinds of substituents, and $R_3$ is only H.

The most related literatures of the present application are the patent literatures concerning antitumor activities filed by Aventis Co. under WO2004/046130, WO2005085231, WO2005/111019 and US2007/0173503, which involve a kind of pyridazinone derivatives of formula

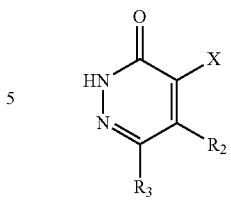

as inhibitors of CDK2, wherein, X is C(O)NHR, NHC(O)R or a heterocycle containing N, $R_2$ is H, and $R_3$ is an aromatic ring or heterocycle.

In addition, pyridazinones are described as inhibitors of RAF kinase in WO2006/124874 for treating tumors, and as inhibitors against tumors in European patent publication 0665223. However, such pyridazinones are totally different from the compounds of the present application.

Moreover, various other pyridazinone derivatives are disclosed in other literatures, and they are different from those in the present application in the selection of substituted groups, moieties and/or 6-positioned aromatic ring groups, or in applications of the compounds.

It is well known that liver cancer is the 5th frequent tumor diseases in males, and the 8th frequent tumor diseases in females. In 2007, it was estimated that 80% patients suffered newly from liver cancer were in developing countries, and 55% of all new patients were in China. In developing countries, among the liver cancer patients, 59% were attributed to HBV, and 33% were attributed to HCV. Particularly, there exists a great market demands for drugs against liver cancer due to the severe HBV infection and increasing incidence of liver cancer in Asia-Pacific countries.

DISCLOSURE OF THE INVENTION

One object of the present invention is to disclose a series of novel pyridazinones having the structure of the following formula I.

Another object of the present invention is to disclose a method for preparing the above pyridazinones.

Still another object of the present invention is to disclose a use of the above pyridazinones in manufacturing an antitumor medicament.

The present invention provides a series of novel pyridazinones having the structure of formula I:

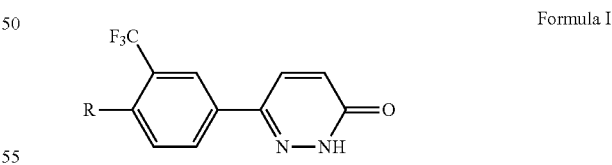

Formula I wherein,

R is —OH, —SH, substituted or unsubstituted $C_6$-$C_{12}$ aryl, substituted or unsubstituted heteroaryl, substituted or unsubstituted $C_1$-$C_{10}$ alkyl, substituted or unsubstituted $C_3$-$C_{10}$ cycloalkyl, substituted or unsubstituted heterocyclic group, —$OR_a$, —$NHR_a$, —$NR_aR_b$, or —$SR_a$, wherein, $R_a$ and $R_b$ are each independently substituted or unsubstituted $C_1$-$C_{10}$ alkyl, substituted or unsubstituted $C_3$-$C_{10}$ cycloalkyl, substituted or unsubstituted $C_6$-$C_{12}$ aryl, substituted or unsubstituted heteroaryl, or substituted or unsubstituted heterocyclic group;

the substituents are selected from the group consisting of halogen, —OH, —NO$_2$, C$_1$-C$_6$ alkyl, carboxyl, C$_1$-C$_6$ alkyloxycarbonyl, C$_6$-C$_{12}$ aryl, —NH$_2$, C$_1$-C$_6$ alkyl substituted amino, hydroxyl substituted C$_1$-C$_6$ alkyl, hydroxyl substituted C$_1$-C$_6$ alkoxyl group, unsubstituted or C$_1$-C$_6$ alkyl substituted heterocyclic group and —CF$_3$;

the heteroaryl is 5- or 6-membered cyclic ring containing 1 to 3 heteroatoms selected from the group consisting of N, O and S;

the heterocyclic group is 3- to 7-membered monocyclic ring or 8-membered bicyclic ring, which may contain 1 to 3 heteroatoms selected from the group consisting of N, O and S, and the heterocyclic group is optionally oxo substitution or sulfido substitution.

Preferably, in the pyridazinones having the structure of formula I,

R is —OH, —SH, substituted or unsubstituted phenyl, substituted or unsubstituted heteroaryl, substituted or unsubstituted C$_1$-C$_{10}$ alkyl, substituted or unsubstituted C$_3$-C$_{10}$ cycloalkyl, substituted or unsubstituted heterocyclic group, —OR$_a$, —NHR$_a$, —NR$_a$R$_b$ or —SR$_a$, wherein, R$_a$ and R$_b$ are each independently substituted or unsubstituted C$_1$-C$_{10}$ alkyl, substituted or unsubstituted C$_3$-C$_{10}$ cycloalkyl, substituted or unsubstituted phenyl, substituted or unsubstituted heteroaryl or substituted or unsubstituted heterocyclic group;

the substituents are selected from the group consisting of halogen, —OH, —NO$_2$, C$_1$-C$_6$ alkyl, carboxyl, C$_1$-C$_6$ alkoxyl carbonyl, phenyl, —NH$_2$, C$_1$-C$_6$ alkyl substituted amino, hydroxyl substituted C$_1$-C$_6$ alkyl, hydroxyl substituted C$_1$-C$_6$ alkoxyl, unsubstituted or C$_1$-C$_4$ alkyl substituted heterocyclic group and —CF$_3$;

the heteroaryl is 5- or 6-membered cyclic ring containing 1 to 3 nitrogen atoms;

the heterocyclic group is 3- to 7-membered monocyclic ring or 8-membered bicyclic ring, which may contain 1 to 3 nitrogen atoms, and the heterocyclic group is optionally oxo substitution or sulfido substitution. More preferably, the pyridazinones are the following specific compounds:

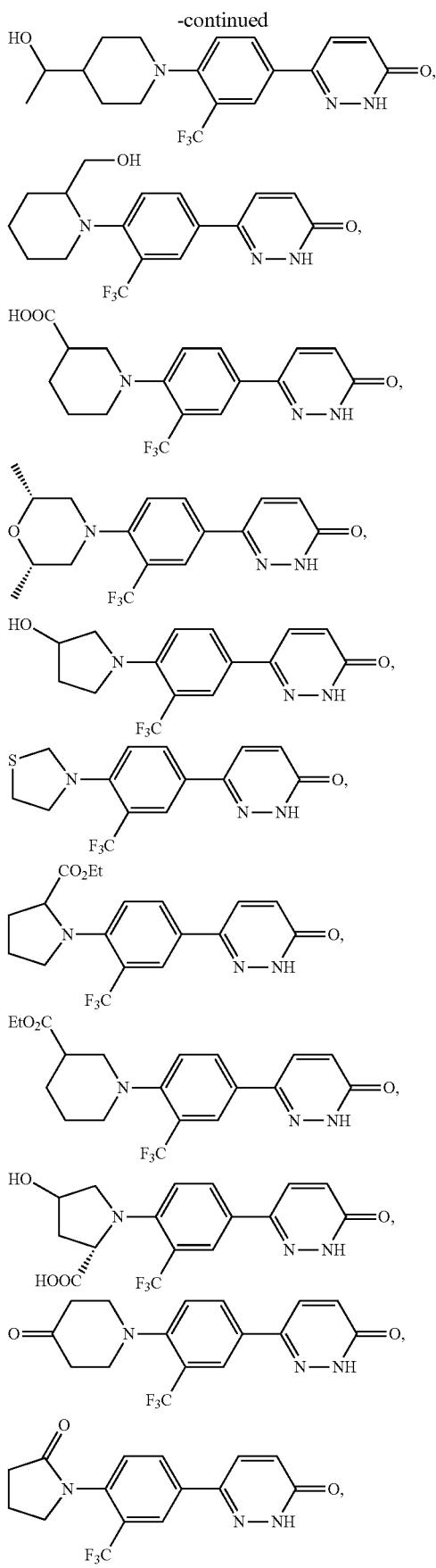

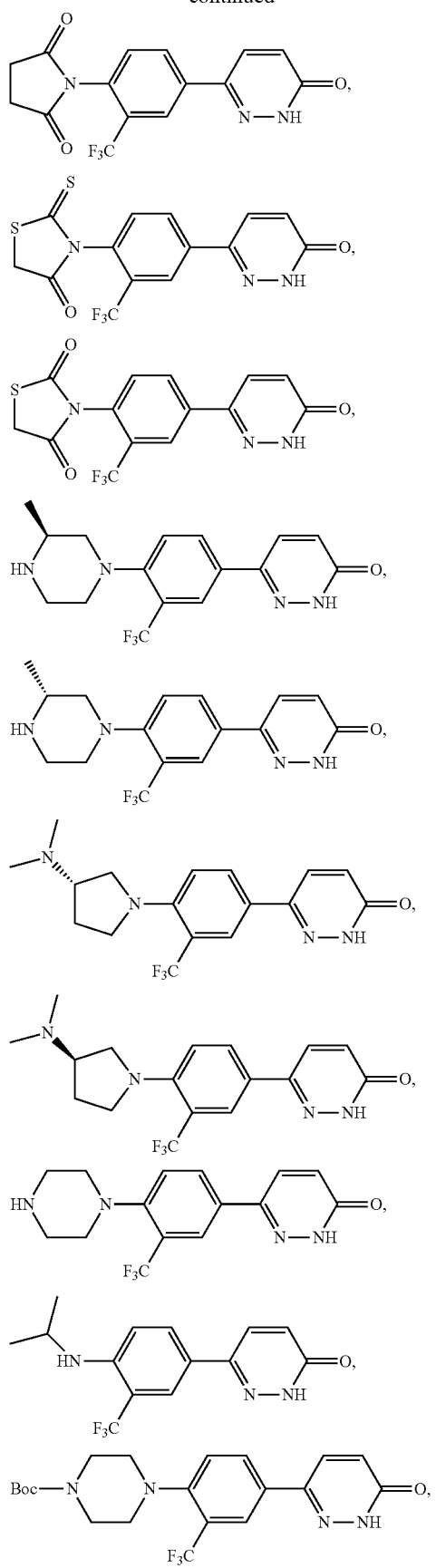

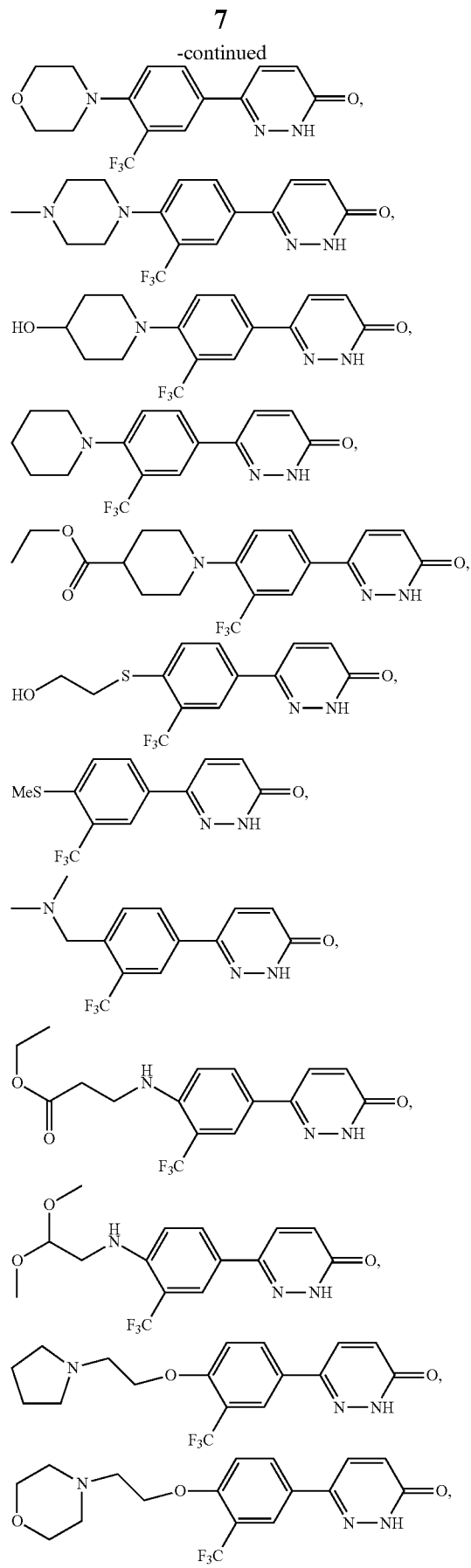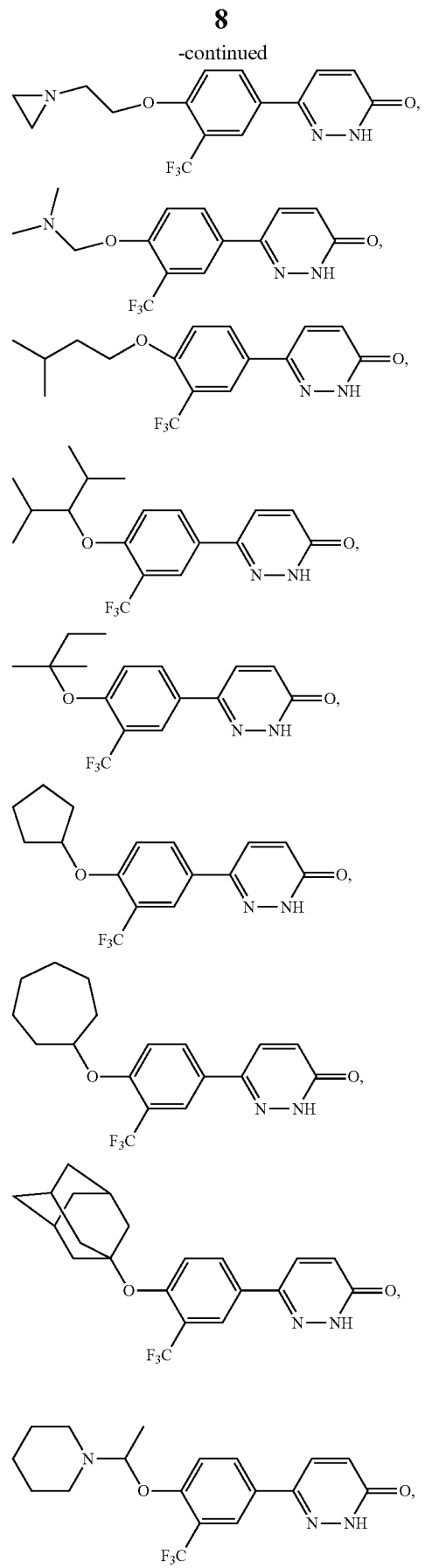

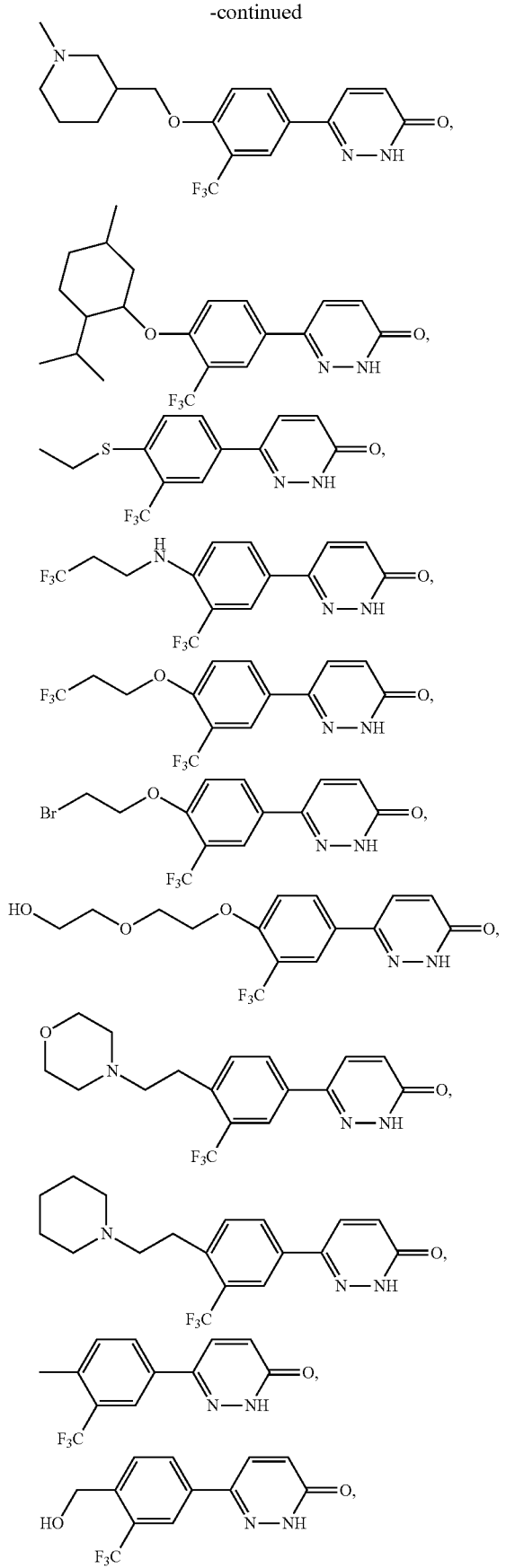
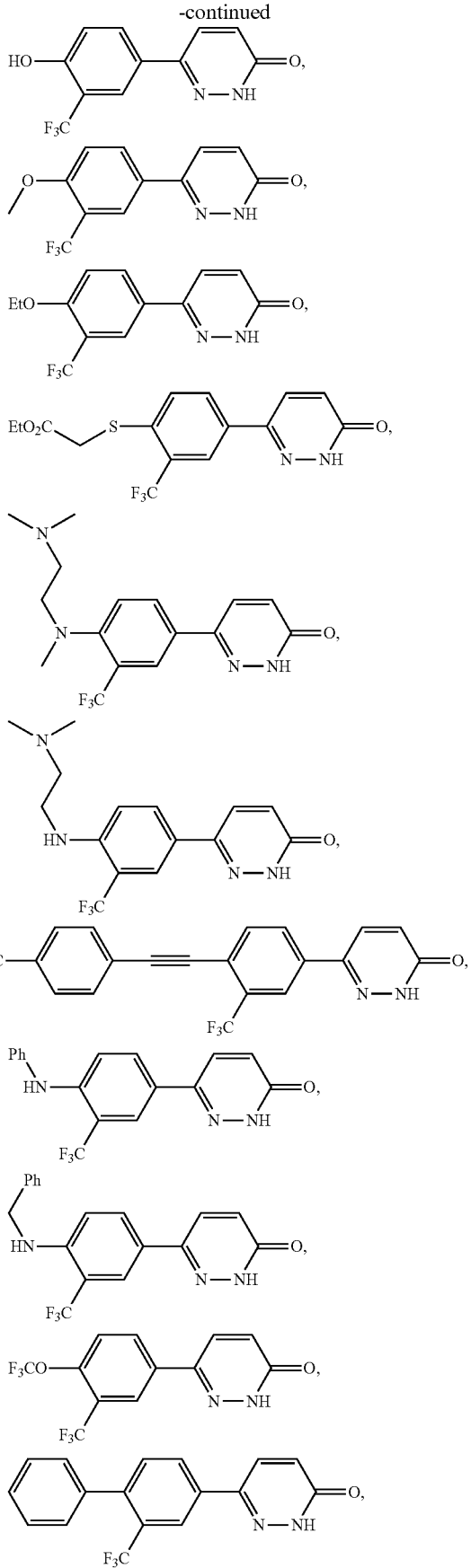

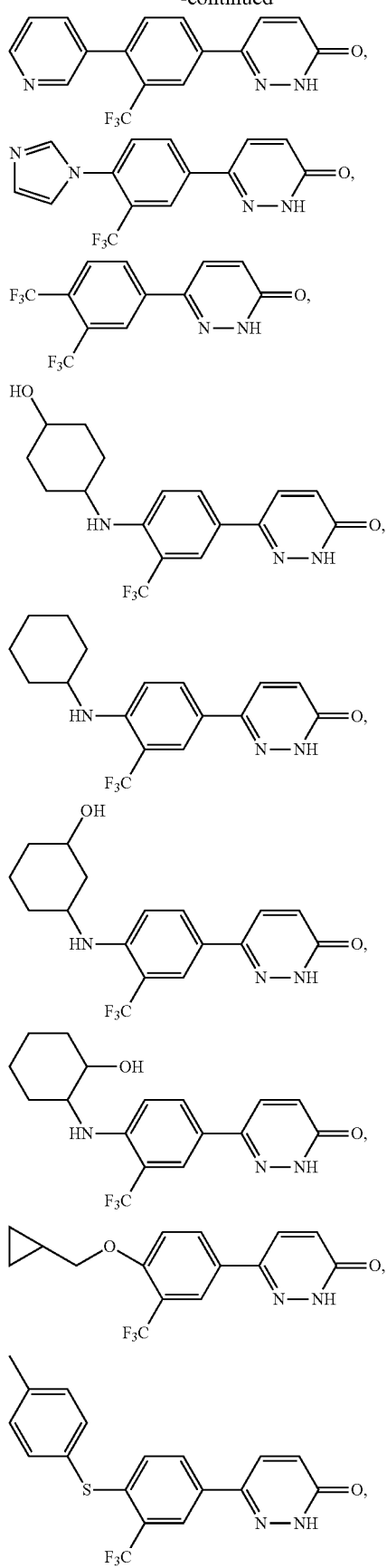

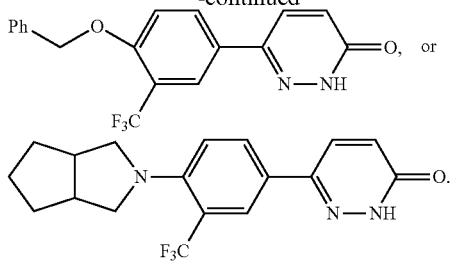

The above pyridazinones exhibit a high activity against tumors, especially, liver cancer. For example, compound YHHU-646 showed a significant curative effect against liver cancer of animals in vivo. In addition, the pyridazinones showed a significant inhibition activity against the proliferation of vascular endothelial cells, indicating that the series of compounds are inhibitors for the proliferation of the vascular endothelial cells, capable of inhibiting tumor angiogenesis, and suggesting they have potential to treat a variety of cancers.

The above pyridazinones may be prepared by reacting various m-trifluoromethylbenzaldehyde with methyl acrylate through a Setter reaction to give a 1,4-dicarbonyl compound, then directly adding a hydrazine compound into the reaction mixture to perform an "one-pot" reaction to form a ring, and finally, dehydrogenating by $CuCl_2 \cdot 2H_2O$ to afford a pyridazinone compound. Alternatively, the desired pyridazinones may be obtained after compounds modified by variously substituted benzene rings were prepared through a coupling reaction.

Specifically, the above pyridazinones may be prepared according to any one of the following methods:

Method 1

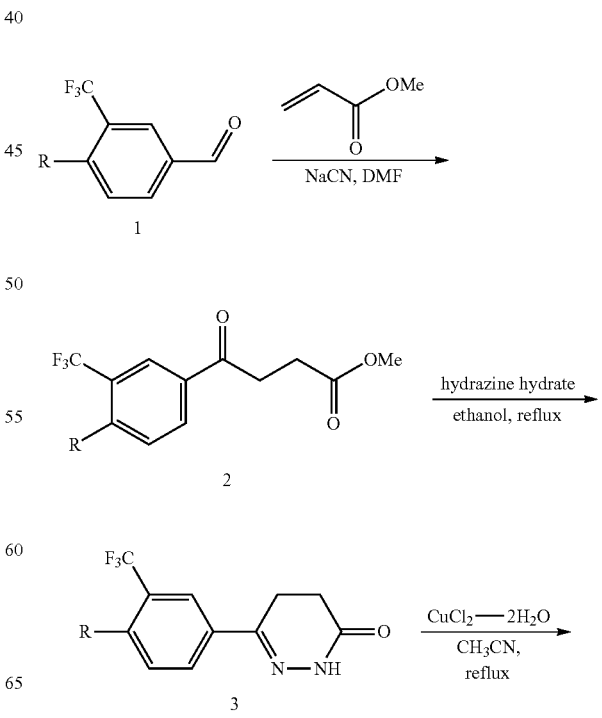

-continued

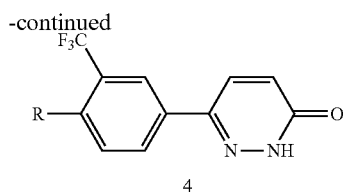

Method 2

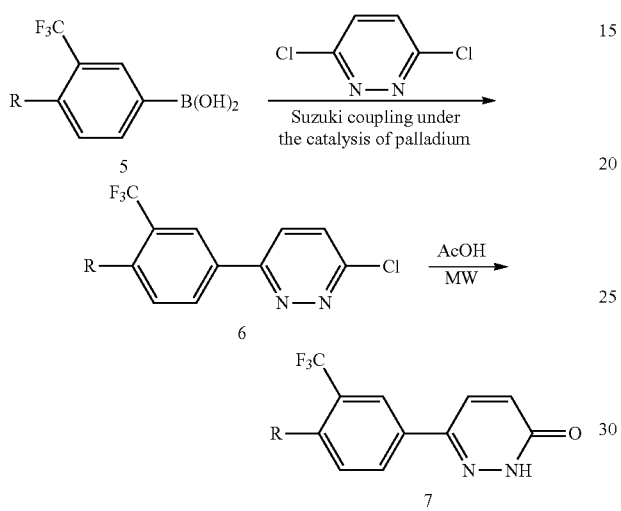

and,

Method 3

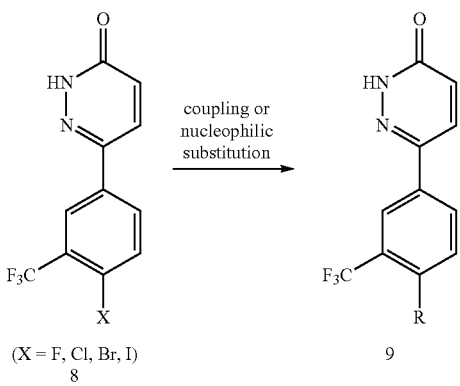

In the above methods, R is —OH, —SH, substituted or unsubstituted $C_6$-$C_{12}$ aryl, substituted or unsubstituted heteroaryl, substituted or unsubstituted $C_1$-$C_{10}$ alkyl, substituted or unsubstituted $C_3$-$C_{10}$cycloalkyl, substituted or unsubstituted heterocyclic group, —$OR_a$, —$NHR_a$, —$NR_aR_b$ or —$SR_a$, wherein, $R_a$ and $R_b$ are each independently substituted or unsubstituted $C_1$-$C_{10}$ alkyl, substituted or unsubstituted $C_3$-$C_{10}$cycloalkyl, substituted or unsubstituted $C_6$-$C_{12}$ aryl, substituted or unsubstituted heteroaryl or substituted or unsubstituted heterocyclic group;

the substituents are selected from the group consisting of halogen, —OH, —$NO_2$, $C_1$-$C_6$ alkyl, carboxyl, $C_1$-$C_6$ alkoxylcarbonyl, $C_6$-$C_{12}$ aryl, —$NH_2$, $C_1$-$C_6$ alkyl substituted amino, hydroxyl substituted $C_1$-$C_6$ alkyl, hydroxyl substituted $C_1$-$C_6$ alkoxyl group, unsubstituted or $C_1$-$C_6$ alkyl substituted heterocyclic group and —$CF_3$;

the heteroaryl is 5- or 6-membered cyclic ring containing 1 to 3 heteroatoms selected from the group consisting of N, O and S;

the heterocyclic group is 3- to 7-membered monocyclic ring or 8-membered bicyclic ring, which may contain 1 to 3 heteroatoms selected from the group consisting of N, O and S, and the heterocyclic group is optionally oxo substitution or sulfido substitution.

Another object of the present invention is to disclose a pharmaceutical composition containing the above pyridazinones. The pharmaceutical composition may contain a therapeutically effective amount of one or more of the above pyridazinones and pharmaceutically acceptable adjuvant(s).

BRIEF DESCRIPTION OF DRAWINGS

FIG. 1 is a graph illustrating the curative effects of the compounds YHHU-744, YHHU-755, YHHU-756, YHHU-759, YHHU-776 and Sorafenib against human liver cancer Bel-7402 transplanted tumor on nude mice.

BEST MODE FOR CARRYING OUT THE INVENTION

The present invention will be further described with reference to the following examples, but the invention is not limited thereto.

Example 1

Preparation of the Key Intermediate 6-(4-fluoro-3-trifluoromethyl)phenyl-pyridazin-3(2H)-one (8F)

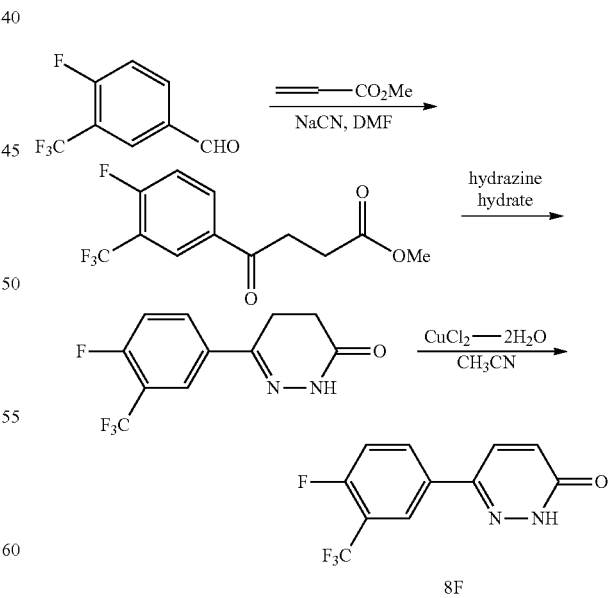

NaCN (24.5 mg, 0.5 mmol) was dissolved in 5 ml of dry DMF at 35° C., and under $N_2$, 4-fluoro-3-trifluoromethyl-benzaldehyde (1.03 g, 5 mmol) was dropped thereinto. After the dropping, stirring continued for 30 minutes. Then, methyl acrylate (0.52 g, 6 mmol) was dropped thereinto. After the mixture was reacted for 4 hours, hydrazine hydrate (0.72 g, 12.5 mmol) was added thereinto directly and the reaction mixture was heated to 60° C. and stirred for 8 hours.

The reaction was quenched, and the temperature was cooled to room temperature. The reaction mixture was added with 20 ml of water, and extracted with ethyl acetate (20 ml×3). The combined organic layer was washed with saturated saline (10 ml×3), dried with anhydrous $Na_2SO_4$, filtrated, and evaporated to dryness in vacuum. The residue was purified by silica gel column chromatography eluting with ethyl acetate-petroleum ether (1:2) to give 6-(4-fluoro-3-trifluoromethyl)phenyl-4,5-dihydro-pyridazin-3(2H)-one as an off-white solid (0.73 g, yield 56%). The solid was dissolved in acetonitrile (10 ml), and $CuCl_2.2H_2O$ (272 mg, 2.02 mmol) was added thereinto. Then the reaction mixture was refluxed for 1 hour under vigorous agitation. After cooled to room temperature, and the reaction mixture was filtered off the remanent $CuCl_2$, and the filtrate was evaporated to dryness under reduced pressure. The residue was added with ethyl acetate (100 mL), washed with saturated $NaHCO_3$ solution (20 ml) and then with saturated saline (20 ml×2), dried with anhydrous $Na_2SO_4$, filtrated, and evaporated to dryness under reduced pressure. The residue was purified by silica gel column chromatography eluting with ethyl acetate-dichloromethane(1:3) to give the target product 8F (130 mg, yield 50%).

$^1$H NMR (DMSO-$d_6$, 300 MHz): δ 11.50 (1H, bs), 8.17 (3H, m), 7.63 (1H, t, J=9.8 Hz), 7.03 (1H, dd, J=5.6, 1.1 Hz).

Example 2

Preparation of 6-m-trifluoromethyl-p-ethylamine phenyl-pyridazin-3(2H)-one (9a)

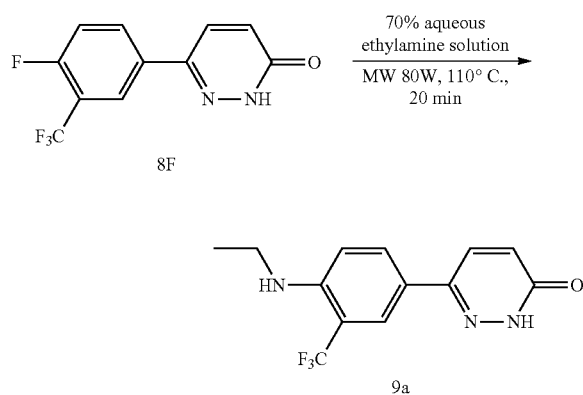

To 8F (100 mg, 0.4 mmol) in a 10 ml microwave vial, was added 3 ml of 70% aqueous ethylamine solution, followed by microwave irradiation (80 W, 110, 20 min). After the reaction completed, the reaction mixture was extracted with ethyl acetate, and the organic layer was dried and concentrated. The residue was purified by silica gel column chromatography eluting with ethyl acetate-dichloromethane (1:2) to give the target product 9a (32.9 mg, yield 30%).

$^1$H NMR (CDCl$_3$, 300 MHz): δ 11.88 (1H, bs), 11.42 (1H, bs), 7.89 (1H, s), 7.80 (1H, s), 7.80 (1H, m), 7.72 (1H, m), 7.05 (1H, d, J=9.6 Hz), 6.79 (1H, d, J=9.6 Hz), 3.28 (2H, q, J=7.2 Hz), 1.34 (3H, t, J=7.2 Hz).

Example 3

Preparation of 6-(4-(2-hydroxyethylamine)-3-trifluoromethylphenyl)-pyridazin-3(2H)-one (9b)

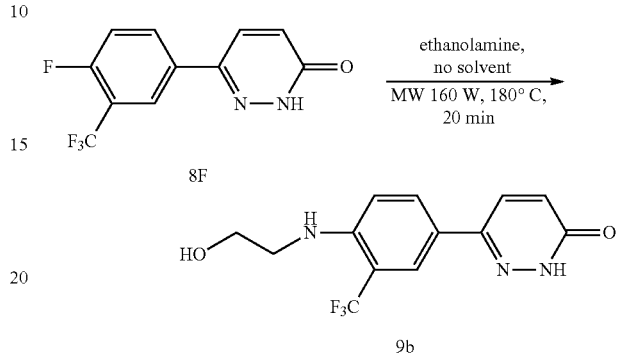

To 8F (100 mg, 0.4 mmol) in a 10 ml microwave vial, was added 3 ml of ethanolamine as a solvent, followed by microwave irradiation (160 W, 180, 20 min). After the reaction was completed, the reaction mixture was extracted with ethyl acetate, and the organic layer was dried and concentrated. The residue was purified by silica gel column chromatography eluting with ethyl acetate-dichloromethane (1:2) to give the target product 9b.

$^1$H NMR (CDCl$_3$, 300 MHz): δ 8.14 (1H, s), 8.12 (1H, d, J=11.3 Hz), 7.63 (3H, m), 7.38 (1H, bs), 6.83 (1H, d, J=9.4 Hz), 4.00 (2H, t, J=4.0 Hz), 3.57 (2H, m).

Example 4

Preparation of 6-(4-(4-methylpiperazinyl)-3-trifluoromethylphenyl)-pyridazin-3(2H)-one (9c)

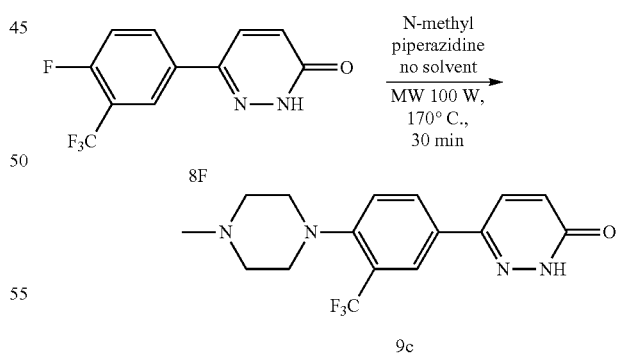

To 8F (100 mg, 0.4 mmol) in a 10 ml microwave vial, was added 3 ml of N-methylpiperazine as a solvent, followed by microwave irradiation (100 W, 170, 30 min). After the reaction was completed, the reaction mixture was extracted with ethyl acetate, and the organic layer was dried and concentrated. The residue was purified by silica gel column chromatography eluting with methanol-dichloromethane (1:10) to give the target product 9c.

¹H NMR (DMSO-d₆, 300 MHz): δ 8.09 (3H, m), 7.59 (1H, d, J=9.5 Hz), 6.98 (1H, d, J=9.8 Hz), 2.90 (4H, t, J=4.0 Hz), 2.44 (4H, m), 2.22 (3H, s).

Example 5

Preparation of 6-(4-methoxy-3-trifluoromethylphenyl)-pyridazin-3(2H)-one (9d)

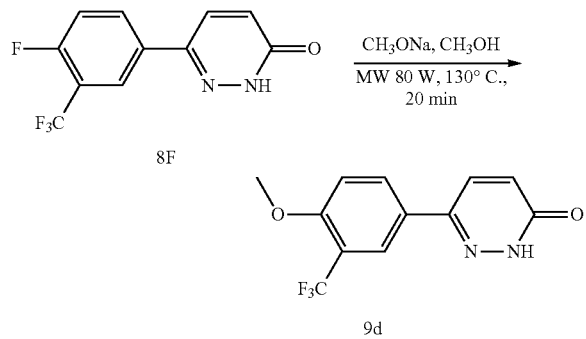

To 8F (100 mg, 0.4 mmol) in a 10 ml microwave vial, was added an excess amount of sodium methoxide in methanol, followed by microwave irradiation (80 W, 130, 20 min). After the reaction was completed, the reaction mixture was extracted with ethyl acetate, and the organic layer was dried and concentrated. The residue was purified by silica gel column chromatography eluting with ethyl acetate-dichloromethane (1:2) to give the target product 9d.

¹H NMR (CDCl₃, 300 MHz): δ 11.43 (1H, bs), 8.01 (1H, s), 7.94 (1H, dd, J=8.8, 1.2 Hz), 7.73 (1H, d, J=9.8 Hz), 7.10 (1H, d, J=8.9 Hz), 7.08 (1H, d, J=10.2 Hz), 3.97 (3H, s).

Example 6

Preparation of 6-(4-(piperid-1-yl)-3-trifluoromethyl phenyl)-pyridazin-3(2H)-one (7a)

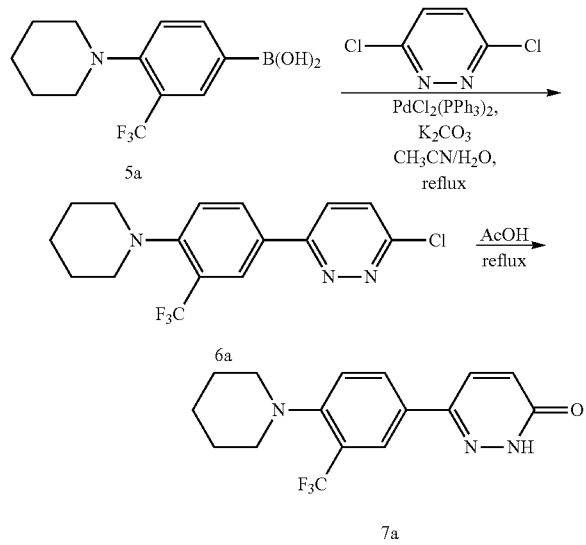

To a mixture of 100 mg of 3,6-dichloropyridazine (0.67 mmol), 1.2 eq of 5a, 1.5 eq of K₂CO₃ and 3 mol % of PdCl₂(PPh₃)₂ in a 25 ml two-necked flask, were added 6 ml of CH₃CN and 4 ml of H₂O. After purged with N₂, the reaction mixture was refluxed and agitated. After the reaction was completed, the mixture was extracted with ethyl acetate, and the organic layer were dried and concentrated. The residue was directly transferred into a 10 ml round necked flask with glacial acetic acid, and refluxed. After the reaction was completed, the reaction mixture was alkalified and extracted with ethyl acetate. The organic layer were dried and concentrated, and the residue was purified through silica gel column chromatography eluting with ethyl acetate-dichloromethane (1:2) to give the target product 7a.

¹H NMR (CDCl₃, 300 MHz): δ 11.38 (1H, bs), 8.02 (1H, d, J=2.1 Hz), 7.90 (1H, dd, J=8.4, 2.4 Hz), 7.75 (1H, d, J=9.9 Hz), 7.36 (1H, d, J=8.8 Hz), 7.08 (1H, d, J=9.9 Hz), 2.90 (4H, t, J=3.3 Hz), 1.72 (4H, m), 1.58 (2H, m).

Example 7

Preparation of 6-(4-(morpholin-1-yl)-3-trifluoromethylphenyl)-pyridazin-3(2H)-one (7b)

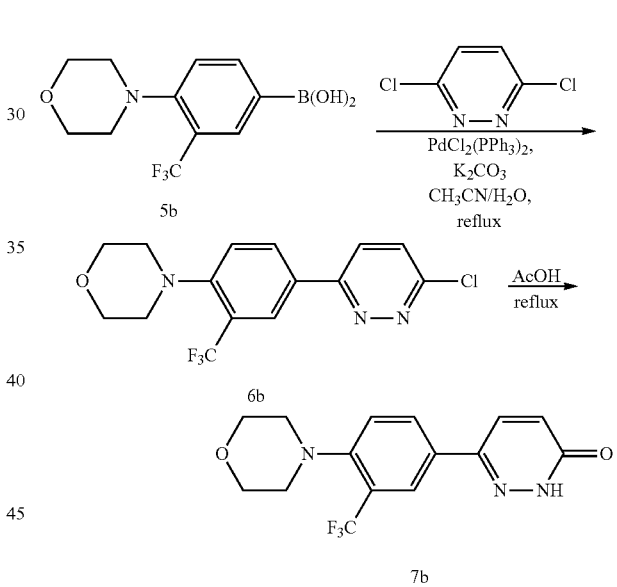

To a mixture of 100 mg of 3,6-dichloropyridazine (0.67 mmol), 1.2 eq of 5b, 1.5 eq of K₂CO₃ and 3 mol % of PdCl₂(PPh₃)₂ in a 25 ml two-necked flask, were added 6 ml of CH₃CN and 4 ml of H₂O. After purged with N₂, the reaction mixture was refluxed and stirred. After the reaction was completed, the mixture was extracted with ethyl acetate, and the organic layer was dried and concentrated. The residue was directly transferred into a 10 ml round necked flask with glacial acetic acid and refluxed. After the reaction was completed, the mixture was alkalified and extracted with ethyl acetate, and the organic layer was dried and concentrated. The residue was purified through silica gel column chromatography eluting with ethyl acetate-dichloromethane (1:1) to give the target product 7b.

¹H NMR (CDCl₃, 300 MHz): δ 12.00 (1H, bs), 8.08 (1H, d, J=1.8 Hz), 7.96 (1H, dd, J=8.4, 1.8 Hz), 7.76 (1H, d, J=9.9 Hz), 7.42 (1H, d, J=8.6 Hz), 7.11 (1H, d, J=9.9 Hz), 3.86 (4H, t, J=4.4 Hz), 2.99 (4H, t, J=4.6 Hz).

Example 8

Preparation of 6-(4-(2-dimethylamino)ethylamino)-3-trifluoromethyl phenyl)-pyridazin-3(2H)-one (9e)

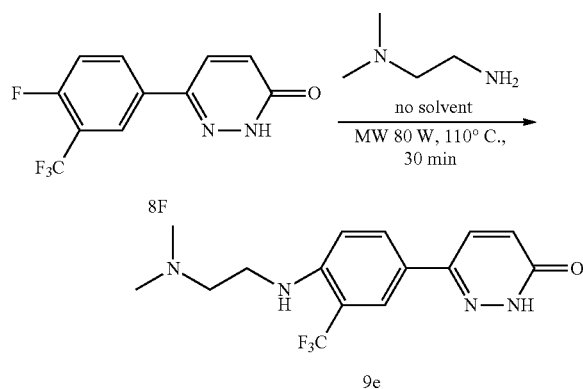

To 8F (100 mg, 0.4 mmol) in a 10 ml microwave vial, was added 3 ml of 2-dimethylaminoethylamine as a solvent, followed by microwave irradiation (80 W, 110, 30 min). After the reaction was completed, the mixture was extracted with ethyl acetate, and the organic layer was dried and concentrated. The residue was purified by silica gel column chromatography eluting with methanol-dichloromethane (1:20) to give the target product 9e.

$^1$H NMR (DMSO-d$_6$, 300 MHz): δ 8.03 (1H, d, J=9.8 Hz), 7.93 (2H, m), 6.94 (1H, d, J=10.0 Hz), 6.92 (1H, d, J=8.5 Hz), 5.67 (1H, d, J=4.2 Hz), 3.26 (2H, dd, J=6.3 Hz), 2.50 (2H, m) 2.19 (6H, s).

Example 9

The Preparation of 6-(4-cyclohexylamino-3-trifluoromethyl phenyl)-pyridazin-3(2H)-one (9f)

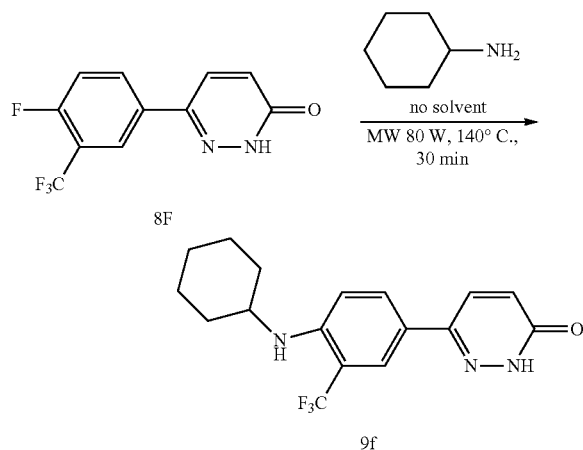

To 8F (100 mg, 0.4 mmol) in a 10 ml microwave vial, was added an excess amount of cyclohexylamine as a solvent, followed by microwave irradiation (80 W, 140, 30 min). After the reaction was completed, the mixture was extracted with ethyl acetate, and the organic layer was dried and concentrated. The residue was purified by silica gel column chromatography eluting with ethyl acetate-dichloromethane (1:2) to give the target product 9f.

$^1$H NMR (CDCl$_3$, 300 MHz): δ 11.26 (1H, bs), 7.86 (1H, d, J=2.1 Hz), 7.77 (1H, dd, J=8.6, 1.8 Hz), 7.69 (1H, d, J=9.8 Hz), 7.04 (1H, d, J=9.8 Hz), 6.81 (1H, d, J=9.0 Hz), 4.49 (1H, d, J=6.5 Hz), 3.43 (1H, bs), 2.05 (2H, m), 1.77 (2H, m), 1.35 (6H, m).

Example 10

Preparation of 6-(4-(4-hydroxypiperidin-1-yl)-3-trifluoromethylphenyl)-pyridazin-3(2H)-one (9g)

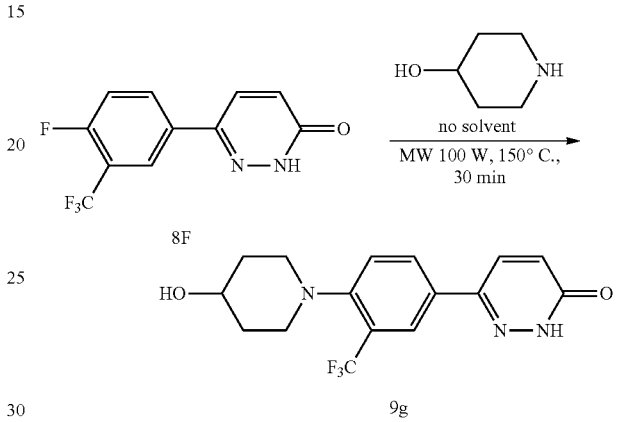

To 8F (100 mg, 0.4 mmol) in a 10 ml microwave vial, was added an excess amount of 4-hydroxypiperidine (no solvent), followed by microwave irradiation (100 W, 150, 30 min). After the reaction was completed, the mixture was extracted with ethyl acetate, and the organic layer was dried and concentrated. The residue was purified by silica gel column chromatography eluting with ethyl acetate-dichloromethane (1:2) to give the target product 9g.

$^1$H NMR (CDCl$_3$, 300 MHz): δ 10.79 (1H, bs), 8.03 (1H, d, J=2.1 Hz), 7.90 (1H, dd, J=8.6, 1.6 Hz), 7.73 (1H, d, J=10.3 Hz), 7.39 (1H, d, J=8.7 Hz), 7.08 (1H, d, J=9.9 Hz), 3.89 (1H, bs), 3.17 (2H, m), 2.84 (2H, m), 2.02 (2H, m), 1.76 (2H, m), 1.45 (1H, d, J=4.0 Hz).

Example 11

Preparation of the Key Intermediate 6-(4-methyl-3-trifluoromethyl)phenyl-pyridazin-3(2H)-one (4a)

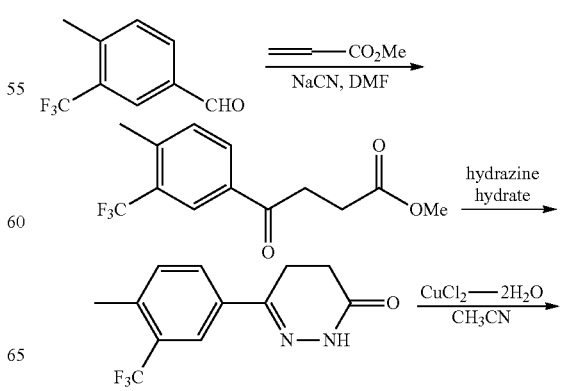

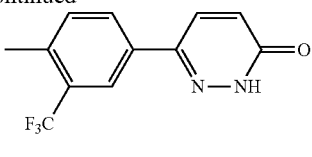

4a

NaCN (24.5 mg, 0.1 eq) was dissolved in 5 ml of dried DMF at 35° C. Under N₂, 4-methyl-3-trifluoromethylbenzaldehyde (1.0 eq) was dropped thereinto. After the dropping, the stirring continued for 30 min, and then methyl acrylate (1.1 eq) was dropped thereinto. After the reaction continued for 4 hours, hydrazine hydrate (5.0 eq) was added thereinto directly. The reaction system was heated to 60 and stirred for 8 hours.

After the reaction was quenched, the reaction system was cooled to room temperature, added with 20 ml of water, and extracted with ethyl acetate (20 ml×3). The combined organic layer was washed with saturated saline (10 ml×3), dried by anhydrous Na₂SO₄, filtrated, and evaporated to dryness in vacuum. The residue was purified by silica gel column chromatography eluting with ethyl acetate-petroleum ether (1:2) to give 6-(4-methyl-3-trifluoromethyl)phenyl-4,5-dihydro-pyridazin-3(2H)-one as an off-white solid. The resulted solid was dissolved in acetonitrile (10 ml), followed by addition of CuCl₂.2H₂O (1.5 eq). The reaction mixture was refluxed for 1 hour under vigorous agitation, cooled to room temperature, and filtrated off the remaining CuCl₂. The filtrate was evaporated to dryness under reduced pressure and the residue was added with ethyl acetate (100 ml), washed with saturated NaHCO₃ solution (20 ml) and then with saturated saline (20 ml×2), dried by anhydrous Na₂SO₄, filtrated and evaporated to dryness under reduced pressure. The residue was purified by silica gel column chromatography eluting with ethyl acetate-dichloromethane (1:2) to give the target product 4a.

¹H NMR (CDCl₃, 300 MHz): δ 11.03 (1H, bs), 8.01 (1H, s), 7.94 (1H, dd, J=8.6, 1.2 Hz), 7.73 (1H, d, J=9.8 Hz), 7.10 (1H, d, J=8.7 Hz), 7.08 (1H, d, J=9.9 Hz), 1.97 (3H, s).

Example 12

Preparation of 6-(4-(N-t-butyloxycarbonylpiperazinyl)-3-trifluoromethyl)phenyl-pyridazin-3(2H)-one (4b)

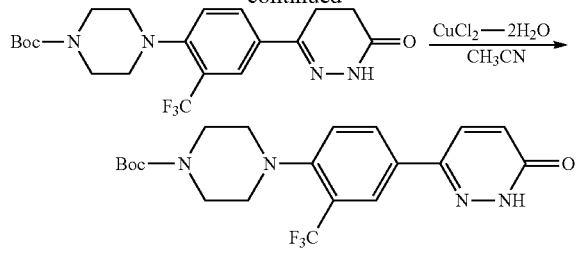

4b

NaCN (24.5 mg, 0.1 eq) was dissolved in 5 ml of dry DMF at 35° C. Under N₂, 4-(N-t-butyloxycarbonylpiperazinyl)-3-trifluoromethylbenzaldehyde (1.0 eq) was dropped thereinto. After the dropping, the stirring continued for 30 min, and then methyl acrylate (1.1 eq) was dropped therein. After the reaction continued for 4 hours, hydrazine hydrate (5.0 eq) was added thereinto directly. The reaction system was heated to 60° C. and stirred for 8 hours The reaction was ceased, and the reaction system was cooled to room temperature, added with 20 ml of water, and extracted with ethyl acetate (20 ml×3). The combined organic layer was washed with saturated saline (10 ml×3), dried by anhydrous Na₂SO₄, filtrated and evaporated to dryness under reduced pressure. The residue was purified by silica gel column chromatography eluting with ethyl acetate-petroleum ether (1:2) to give 6-(4-(N-t-butyloxycarbonylpiperazinyl)-3-trifluoromethyl)phenyl-4,5-dihydro-pyridazin-3(2H)-one. The resultant solid was dissolved in acetonitrile (10 ml), followed by addition of CuCl₂.2H₂O (1.5 eq). The reaction was refluxed for 1 hour under vigorous agitation. After cooled to room temperature, the reaction mixture was filtrated off the remaining CuCl₂, and the filtrate was evaporated to dryness under reduced pressure. The residue was added with ethyl acetate (100 ml). The solution was washed with saturated NaHCO₃ solution (20 ml) and then with saturated saline (20 ml×2), dried by anhydrous Na₂SO₄, filtrated and evaporated to dryness under reduced pressure. The residue was separated by silica gel column chromatography eluting with ethyl acetate-dichloromethane (1:2) to give the target product 4b.

¹H NMR (DMSO-d₆, 300 MHz): δ 13.27 (1H, bs), 8.12 (3H, m), 7.65 (1H, d, J=8.8 Hz), 7.01 (1H, dd, J=1.9, 9.9 Hz), 3.45 (4H, m), 2.87 (4H, m), 1.43 (9H, s).

Example 13

Preparation of 6-(4-p-trifluoromethylphenylacetenyl-3-trifluoromethyl)phenyl-pyridazin-3(2H)-one (9h)

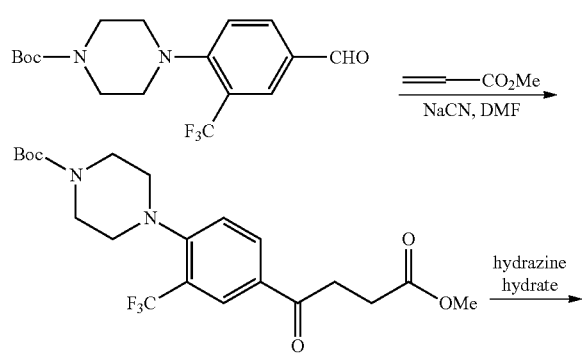

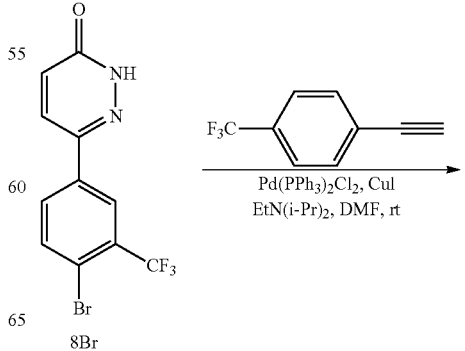

8Br

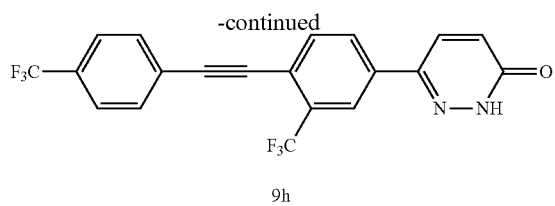

9h

To a mixture of 8Br (50 mg, 0.18 mmol), 5 mol % PdCl$_2$(PPh$_3$)$_2$ and 5 mol % CuI in a dry two-necked flask under N$_2$, were added 5 eq of EtN(i-Pr)$_2$ and 1.2 eq of p-trifluoromethylphenylacetylene, followed by addition of redistilled dry DMF. After the reaction at 30 was finished, the reaction mixture was extracted with ethyl acetate, and the organic layer was dried and concentrated. The residue was separated by silica gel column chromatography eluting with ethyl acetate-petroleum ether (1:2) to give the target product 9h.

$^1$H NMR(CDCl$_3$, 300 MHz): δ 12.05 (1H, bs), 8.04 (1H, s), 8.17 (2H, m), 7.58 (1H, d, J=7.6 Hz), 7.32 (2H, d, J=8.9 Hz), 7.40 (2H, d, J=8.9 Hz), 7.08 (1H, d, J=7.6 Hz).

Example 14

Preparation of 6-(4-phenyl-3-trifluoromethyl)phenyl-pyridazin-3(2H)-one (9i)

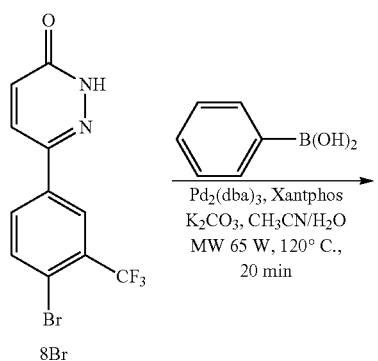

8Br

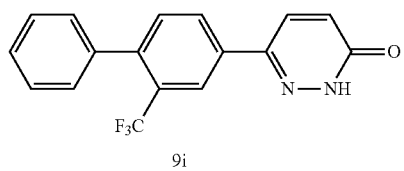

9i

To a mixture of 8Br (50 mg, 0.18 mmol), 1.2 eq of phenylboric acid, 1.5 mol % of Pd$_2$(dba)$_3$, 3.0 mol % of Xantphos (4,5-bi(diphenylphosphino)-9,9-dimethylxanthene) and 3 eq of K$_2$CO$_3$ in a 10 ml microwave vial, were added 1.5 ml of CH$_3$CN and 1.0 ml of H$_2$O. After purged with N$_2$, the reaction mixture was subjected to a microwave treatment (65 W, 120, 20 min). After the reaction was completed, the mixture was extracted with ethyl acetate, and the organic layer was dried and concentrated. The residue was separated by silica gel column chromatography eluting with ethyl acetate-petroleum ether (1:2) to give the target product 9i.

$^1$H NMR(CDCl$_3$, 300 MHz): δ 13.00 (1H, bs), 8.04 (1H, s), 7.90 (2H, m), 7.58 (1H, d, J=7.9 Hz), 7.35 (5H, m), 7.08 (1H, d, J=7.9 Hz).

Example 15

Antineoplasmic Activity In Vitro

Protocol: the antineoplasmic activities in vitro of the compounds were assayed by a Sulforhodamine B (SRB) protocol. Tumor cells were cultivated at 37 under 5% CO$_2$ in a RPMI 1640 medium or a DMEM medium (Gibco) containing 10% fetal bovine serum. Tumor cells were inoculated on a 96-well plate with a concentration of 0.4-1.0×10$^4$ cells per well according to the cell types. 24 hours later, the target compounds diluted 10 times were added, each compound having at least 5 concentrations. After treated by the compounds for 72 hours, the culture media were discarded, and the cells were fixed by 10% cold trichloroacetic acid, and then stained by Sulforhodamine B (SRB) solution. The uncombined SRB was washed off, and the SRB combined with protein was dissolved with Tris. OD values were recorded at 515 nm on an ELISA Reader, and the cell growth inhibition rate was calculated according to following equation:

Inhibition rate=$(OD_{control}-OD_{experimental})/OD_{control}$×100%

IC$_{50}$ (50% inhibitory concentration) was calculated by using Logit method based on the inhibition rates at various concentration, and the results are shown in tables 1 and 2.

TABLE 1

The effect of YHU-646 against proliferation of various tumor cells cultivated in vitro.

| Cell line | Types of tumor | IC$_{50}$(μM) YHHU-646 |
|---|---|---|
| SK-OV-3 | ovarian cancer | 0.003 |
| MDA-MB-231 | breast carcinoma | >20 |
| A498 | renal carcinoma | 4.12 |
| HT-29 | colon carcinoma | 6.3 |
| NCI-H460 | lung cancer | 24.1 |
| A549 | lung cancer | — |
| SIMM-7721 | liver cancer | <0.1 |
| SW-620 | colon carcinoma | 5.8 |
| Bel-7402 | liver cancer | 0.0007 |
| SK-BR-3 | breast carcinoma | 7.5 |
| HUVEC | human umbilical vein endothelial cells (normal cells) | 0.03 |

TABLE 2

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-755 | *(structure)* | 324 | Method 1, 2 | <0.01 |
| YHHU-756 | *(structure)* | 339 | Method 1, 2 | <0.01 |
| YHHU-757 | *(structure)* | 338 | Method 1, 2 | <0.01 |
| YHHU-758 | *(structure)* | 270 | Method 1, 2 | <0.01 |
| YHHU-759 | *(structure)* | 326 | Method 1, 2 | <0.01 |
| YHHU-760 | *(structure)* | 300 | Method 3 | >0.1 |
| YHHU-761 | *(structure)* | 298 | Method 1, 2 | <0.01 |
| YHHU-762 | *(structure)* | 271 | Method 3 | <0.01 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-776 | (structure) | 340 | Method 1, 2 | <0.01 |
| YHHU-646 | (structure) | 310 | Method 1, 2 | <0.01 |
| YHHU-647 | (structure) | 284 | Method 1, 2 | <0.01 |
| YHHU-744 | (structure) | 284 | Method 3 | <0.01 |
| YHHU-745 | (structure) | 327 | Method 3 | >1 |
| YHHU-746 | (structure) | 341 | Method 3 | >1 |
| YHHU-747 | (structure) | 338 | Method 1, 2 | <0.01 |
| YHHU-748 | (structure) | 296 | Method 1, 2 | <0.01 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
| --- | --- | --- | --- | --- |
| YHHU-751 | 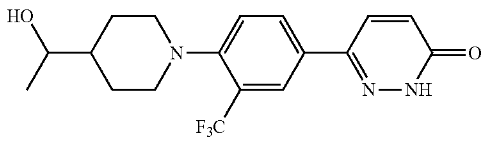 | 368 | Method 1, 3 | <0.01 |
| YHHU-752 | 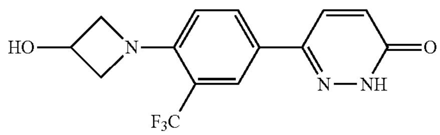 [SMILES: O=c1ccc(-c2ccc(N3CC(O)C3)c(C(F)(F)F)c2)n[nH]1] | 312 | Method 1, 3 | <0.1 |
| YHHU-753 | 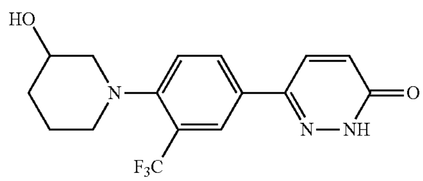 [SMILES: O=c1ccc(-c2ccc(N3CCCC(O)C3)c(C(F)(F)F)c2)n[nH]1] | 340 | Method 1, 3 | <0.1 |
| YHHU-763 | 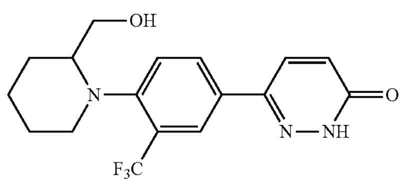 [SMILES: O=c1ccc(-c2ccc(N3CCCCC3CO)c(C(F)(F)F)c2)n[nH]1] | 354 | Method 1, 3 | <0.1 |
| YHHU-765 | 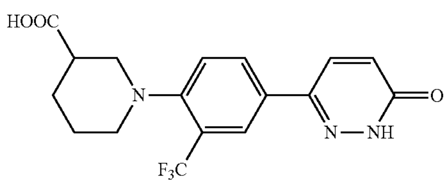 | 368 | Method 1, 3 | <0.1 |
| YHHU-766 | 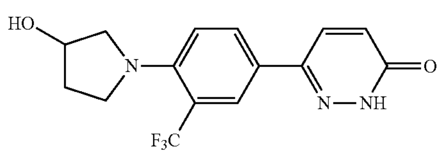 [SMILES: O=c1ccc(-c2ccc(N3CCC(O)C3)c(C(F)(F)F)c2)n[nH]1] | 326 | Method 1, 3 | <0.1 |
| YHHU-768 | 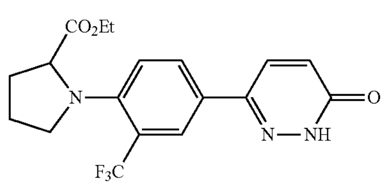 | 382 | Method 1, 3 | <0.1 |
| YHHU-666 | 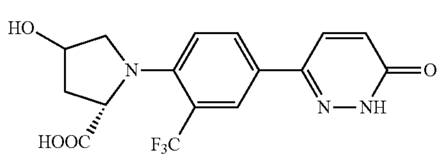 [SMILES: O=C(O)[C@@H]1CC(O)CN1c1ccc(-c2ccc(=O)[nH]n2)cc1C(F)(F)F] | 370 | Method 1, 3 | <1 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-667 | 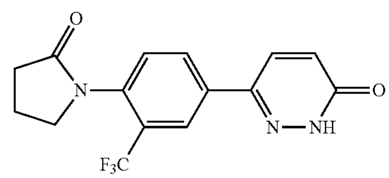 [SMILES: O=C1CCCN1c1ccc(-c2ccc(=O)[nH]n2)cc1C(F)(F)F] | 324 | Method 1, 2 | <0.1 |
| YHHU-668 | 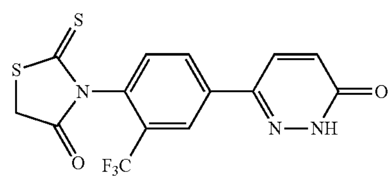 [SMILES: O=C1CSC(=S)N1c1ccc(-c2ccc(=O)[nH]n2)cc1C(F)(F)F] | 372 | Method 1, 2 | <1 |
| YHHU-669 | 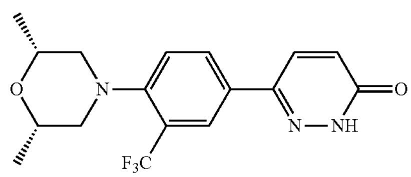 [SMILES: C[C@@H]1CN(c2ccc(-c3ccc(=O)[nH]n3)cc2C(F)(F)F)C[C@H](C)O1] | 354 | Method 1, 2 | <0.01 |
| YHHU-670 | 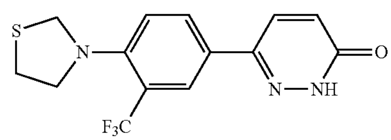 | 328 | Method 1, 2 | <1 |
| YHHU-671 | 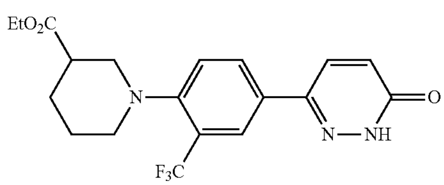 [SMILES: CCOC(=O)C1CCCN(c2ccc(-c3ccc(=O)[nH]n3)cc2C(F)(F)F)C1] | 396 | Method 1, 2 | <0.01 |
| YHHU-672 | 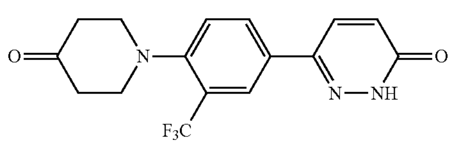 | 338 | Method 1, 2 | <0.1 |
| YHHU-673 | 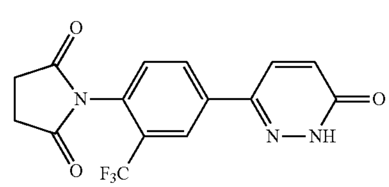 | 338 | Method 1, 2 | <1 |
| YHHU-674 | 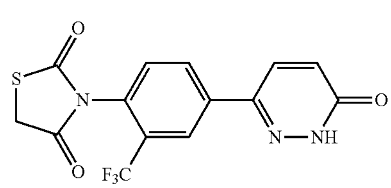 | 356 | Method 1, 2 | <1 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-675 | 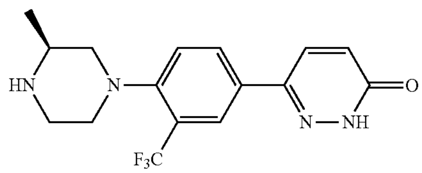 [SMILES: C[C@H]1CN(c2ccc(-c3ccc(=O)[nH]n3)cc2C(F)(F)F)CCN1] | 339 | Method 1, 2 | <0.01 |
| YHHU-676 | 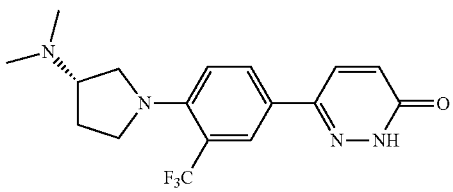 [SMILES: CN(C)[C@H]1CCN(c2ccc(-c3ccc(=O)[nH]n3)cc2C(F)(F)F)C1] | 353 | Method 1, 2 | <0.01 |
| YHHU-677 | 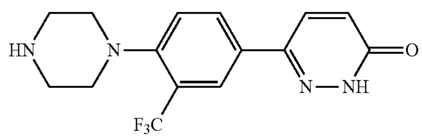 [SMILES: O=c1ccc(-c2ccc(N3CCNCC3)c(C(F)(F)F)c2)n[nH]1] | 325 | Method 1, 2 | <0.1 |
| YHHU-678 | 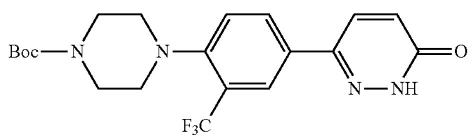 | 425 | Method 1, 2 | <0.01 |
| YHHU-679 | 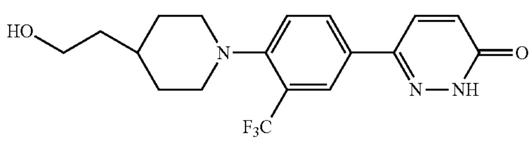 [SMILES: O=c1ccc(-c2ccc(N3CCC(CCO)CC3)c(C(F)(F)F)c2)n[nH]1] | 368 | Method 1 | <0.1 |
| YHHU-681 | 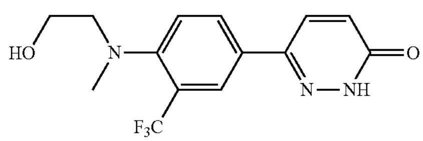 [SMILES: CN(CCO)c1ccc(-c2ccc(=O)[nH]n2)cc1C(F)(F)F] | 314 | Method 1 | <1 |
| YHHU-682 | 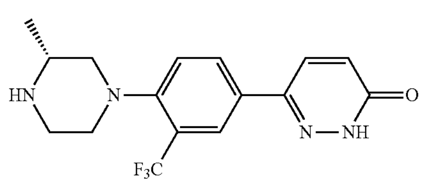 [SMILES: C[C@@H]1CN(c2ccc(-c3ccc(=O)[nH]n3)cc2C(F)(F)F)CCN1] | 339 | Method 1 | <0.01 |
| YHHU-683 | 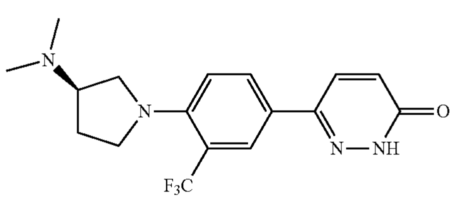 [SMILES: CN(C)[C@@H]1CCN(c2ccc(-c3ccc(=O)[nH]n3)cc2C(F)(F)F)C1] | 353 | Method 1 | <0.1 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-685 | 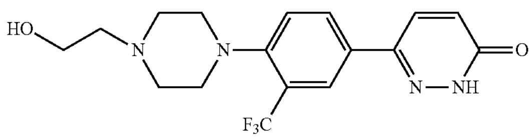 | 369 | Method 3 | <0.01 |
| YHHU-688 | 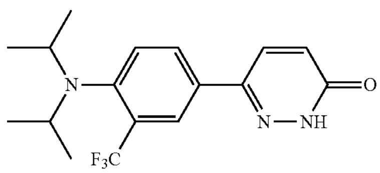 [SMILES: CC(C)N(c1ccc(-c2ccc(=O)[nH]n2)cc1C(F)(F)F)C(C)C] | 340 | Method 1, 2 | <0.01 |
| YHHU-689 | 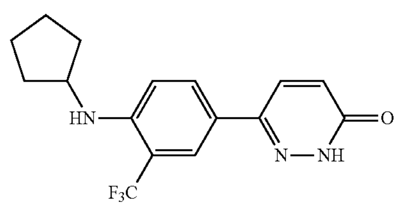 | 324 | Method 3 | <0.1 |
| YHHU-693 | 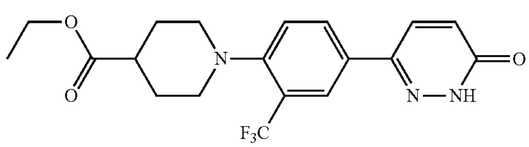 [SMILES: CCOC(=O)C1CCN(c2ccc(-c3ccc(=O)[nH]n3)cc2C(F)(F)F)CC1] | 396 | Method 1, 3 | <0.1 |
| YHHU-694 | 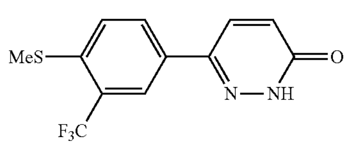 [SMILES: CSc1ccc(-c2ccc(=O)[nH]n2)cc1C(F)(F)F] | 287 | Method 3 | <0.1 |
| YHHU-696 | 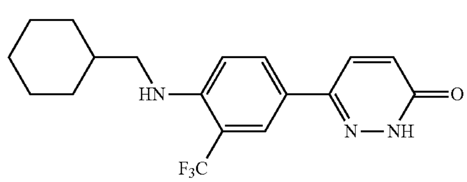 [SMILES: O=c1ccc(-c2ccc(NCC3CCCCC3)c(C(F)(F)F)c2)n[nH]1] | 352 | Method 3 | <0.1 |
| YHHU-700 | 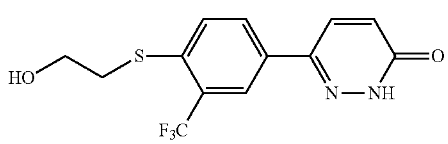 | 317 | Method 1, 2 | <10 |
| YHHU-701 | 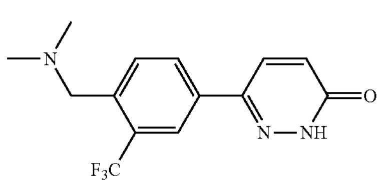 [SMILES: CN(C)Cc1ccc(-c2ccc(=O)[nH]n2)cc1C(F)(F)F] | 298 | Method 1, 2 | <0.01 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-769 | 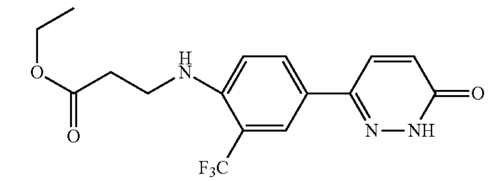 [SMILES: CCOC(=O)CCNc1ccc(-c2ccc(=O)[nH]n2)cc1C(F)(F)F] | 356 | Method 1, 2 | <1 |
| YHHU-770 | 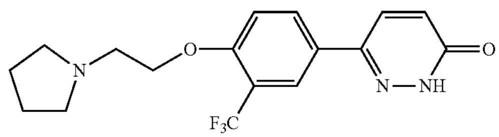 | 354 | Method 1, 2 | <0.1 |
| YHHU-771 | 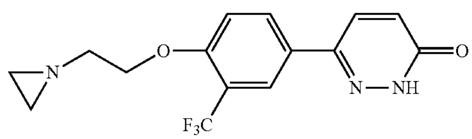 [SMILES: O=c1ccc(-c2ccc(OCCN3CC3)c(C(F)(F)F)c2)n[nH]1] | 326 | Method 1, 2 | <0.1 |
| YHHU-772 | 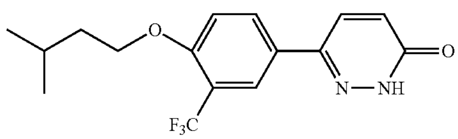 [SMILES: CC(C)CCOc1ccc(-c2ccc(=O)[nH]n2)cc1C(F)(F)F] | 327 | Method 1, 2 | <0.1 |
| YHHU-773 | 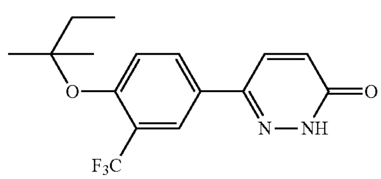 [SMILES: CCC(C)(C)Oc1ccc(-c2ccc(=O)[nH]n2)cc1C(F)(F)F] | 327 | Method 1, 2 | <0.1 |
| YHHU-774 | 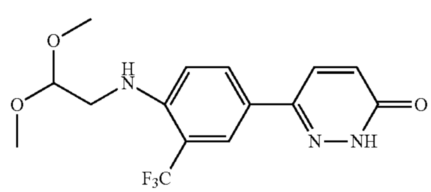 [SMILES: COC(CNc1ccc(-c2ccc(=O)[nH]n2)cc1C(F)(F)F)OC] | 344 | Method 1, 3 | <0.1 |
| YHHU-775 | 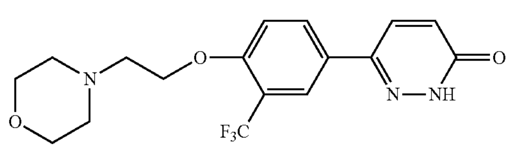 [SMILES: O=c1ccc(-c2ccc(OCCN3CCOCC3)c(C(F)(F)F)c2)n[nH]1] | 370 | Method 1, 2 | <0.1 |
| YHHU-501 | 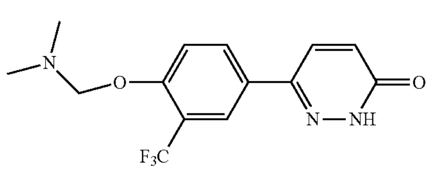 | 314 | Method 1, 2 | <0.1 |

TABLE 2-continued
The synthesis methods and effects on proliferation of human liver cancer cells BEL-7402 cultivated in vitro of some compounds
| No. | Structure | M + 1 peak | Synthesis Method | The Inhibition Activities for Human Liver Cancer Cells BEL-7402 (IC50, μM) |
| --- | --- | --- | --- | --- |
| YHHU-502 | 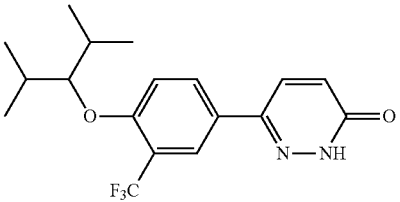 [SMILES: CC(C)C(Oc1ccc(-c2ccc(=O)[nH]n2)cc1C(F)(F)F)C(C)C] | 355 | Method 1, 2 | <0.1 |
| YHHU-503 | 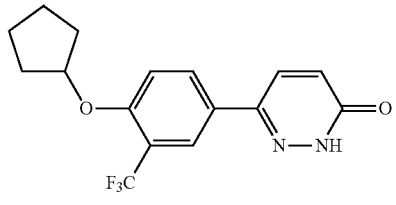 [SMILES: O=c1ccc(-c2ccc(OC3CCCC3)c(C(F)(F)F)c2)n[nH]1] | 325 | Method 1, 2 | <0.1 |
| YHHU-598 | 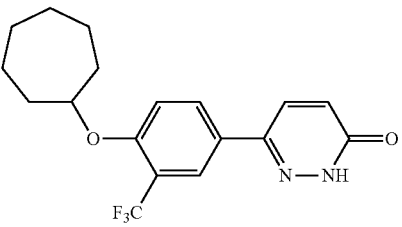 [SMILES: O=c1ccc(-c2ccc(OC3CCCCCC3)c(C(F)(F)F)c2)n[nH]1] | 353 | Method 1, 2 | <0.1 |
| YHHU-597 | 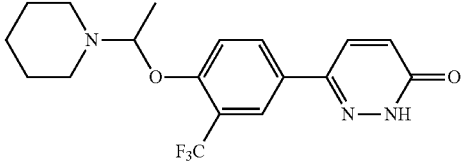 [SMILES: CC(Oc1ccc(-c2ccc(=O)[nH]n2)cc1C(F)(F)F)N1CCCCC1] | 368 | Method 1, 2 | <0.1 |
| YHHU-595 | 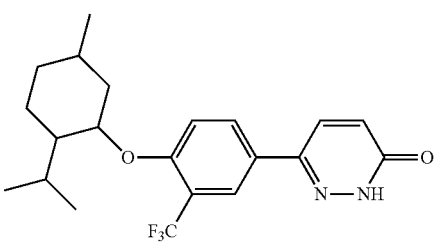 [SMILES: CC1CCC(C(C)C)C(Oc2ccc(-c3ccc(=O)[nH]n3)cc2C(F)(F)F)C1] | 395 | Method 1, 2 | <0.1 |
| YHHU-593 | 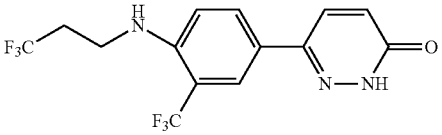 [SMILES: O=c1ccc(-c2ccc(NCCC(F)(F)F)c(C(F)(F)F)c2)n[nH]1] | 322 | Method 1, 3 | <0.1 |

TABLE 2-continued
The synthesis methods and effects on proliferation of human liver cancer cells BEL-7402 cultivated in vitro of some compounds
| No. | Structure | M + 1 peak | Synthesis Method | The Inhibition Activities for Human Liver Cancer Cells BEL-7402 (IC50, μM) |
|---|---|---|---|---|
| YHHU-592 | 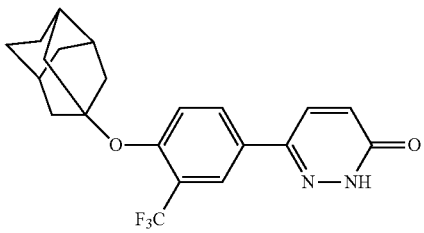 [SMILES: O=c1ccc(-c2ccc(OC34CC5CCC(C3)C(C5)C4)c(C(F)(F)F)c2)n[nH]1] | 391 | Method 1, 2 | <0.1 |
| YHHU-590 | 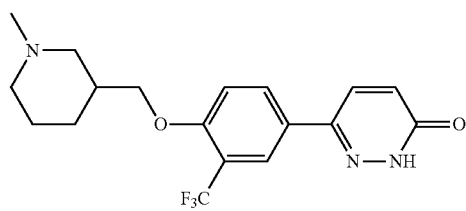 [SMILES: CN1CCCC(COc2ccc(-c3ccc(=O)[nH]n3)cc2C(F)(F)F)C1] | 368 | Method 1, 2 | <0.1 |
| YHHU-589 | 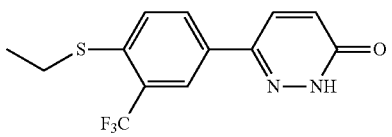 | 301 | Method 1, 2 | <0.1 |
| YHHU-586 | 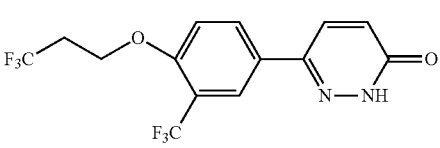 | 353 | Method 1, 2 | <0.1 |
| YHHU-585 | 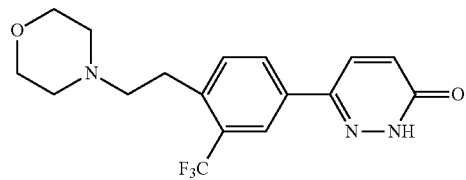 [SMILES: O=c1ccc(-c2ccc(CCN3CCOCC3)c(C(F)(F)F)c2)n[nH]1] | 354 | Method 1, 2 | <0.1 |
| YHHU-581 | 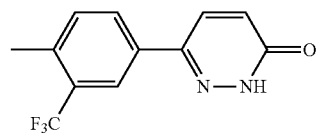 | 255 | Method 1 | <0.1 |
| YHHU-580 | 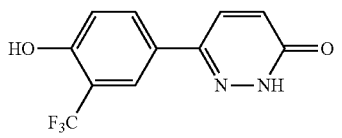 [SMILES: O=c1ccc(-c2ccc(O)c(C(F)(F)F)c2)n[nH]1] | 257 | Method 1 | <0.1 |
| YHHU-579 | 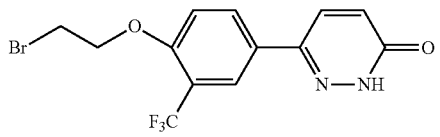 | 364 | Method 1 | <0.1 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-582 | HO-CH2CH2-O-CH2CH2-O-[3-CF3-phenyl]-pyridazinone | 345 | Method 1 | <0.1 |
| YHHU-578 | EtO-[3-CF3-phenyl]-pyridazinone | 285 | Method 1, 2 | <0.1 |
| YHHU-575 | piperidinyl-CH2CH2-[3-CF3-phenyl]-pyridazinone | 352 | Method 1, 2 | <0.1 |
| YHHU-574 | HOCH2-[3-CF3-phenyl]-pyridazinone | 271 | Method 1, 2 | <0.1 |
| YHHU-546 | MeO-[3-CF3-phenyl]-pyridazinone | 271 | Method 3 | <0.1 |
| YHHU-532 | EtO2C-CH2-S-[3-CF3-phenyl]-pyridazinone | 359 | Method 1, 2 | <0.1 |
| YHHU-658 | Ph-NH-[3-CF3-phenyl]-pyridazinone | 332 | Method 3 | <0.1 |
| YHHU-659 | PhCH2-NH-[3-CF3-phenyl]-pyridazinone | 346 | Method 3 | <0.1 |
| YHHU-702 | F3C-phenyl-C≡C-[3-CF3-phenyl]-pyridazinone | 409 | Method 3 | <10 |

TABLE 2-continued
The synthesis methods and effects on proliferation of human liver cancer cells BEL-7402 cultivated in vitro of some compounds
| No. | Structure | M + 1 peak | Synthesis Method | The Inhibition Activities for Human Liver Cancer Cells BEL-7402 (IC50, μM) |
|---|---|---|---|---|
| YHHU-703 | 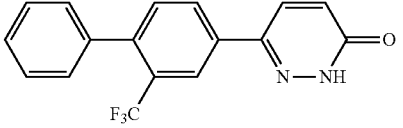 | 317 | Method 3 | <10 |
| YHHU-706 | 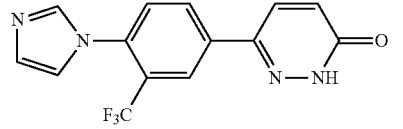 | 307 | Method 1, 3 | <10 |
| YHHU-707 | 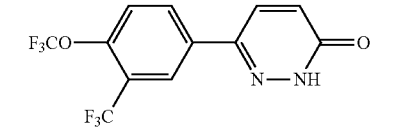 [SMILES: O=c1ccc(-c2ccc(OC(F)(F)F)c(C(F)(F)F)c2)n[nH]1] | 325 | Method 1, 2 | <10 |
| YHHU-709 | 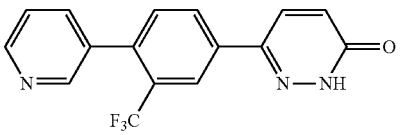 [SMILES: O=c1ccc(-c2ccc(-c3cccnc3)c(C(F)(F)F)c2)n[nH]1] | 318 | Method 3 | <10 |
| YHHU-710 | 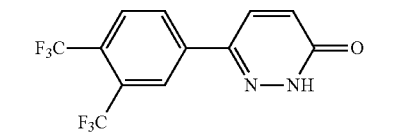 [SMILES: O=c1ccc(-c2ccc(C(F)(F)F)c(C(F)(F)F)c2)n[nH]1] | 309 | Method 2 | <10 |
| YHHU-711 | 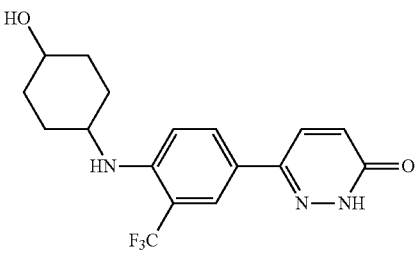 [SMILES: O=c1ccc(-c2ccc(NC3CCC(O)CC3)c(C(F)(F)F)c2)n[nH]1] | 354 | Method 1, 3 | <1 |
| YHHU-712 | 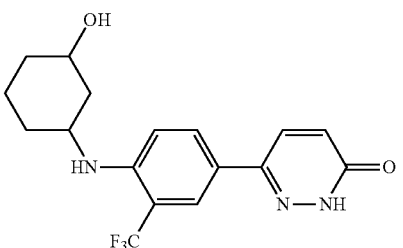 | 354 | Method 1, 3 | <1 |
| YHHU-713 | 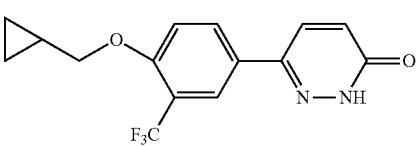 | 311 | Method 3 | <1 |

TABLE 2-continued

The synthesis methods and effects on proliferation of human liver cancer cells BEL-7402 cultivated in vitro of some compounds

| No. | Structure | M + 1 peak | Synthesis Method | The Inhibition Activities for Human Liver Cancer Cells BEL-7402 (IC50, μM) |
|---|---|---|---|---|
| YHHU-714 | 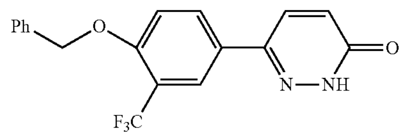 [SMILES: O=c1ccc(-c2ccc(OCc3ccccc3)c(C(F)(F)F)c2)n[nH]1] | 347 | Method 3 | <10 |
| YHHU-715 | 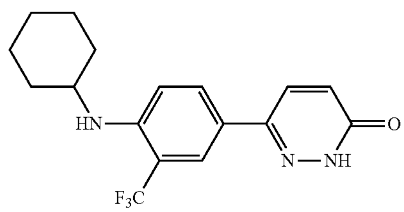 [SMILES: O=c1ccc(-c2ccc(NC3CCCCC3)c(C(F)(F)F)c2)n[nH]1] | 338 | Method 1, 3 | <10 |
| YHHU-716 | 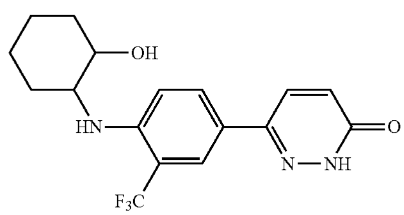 [SMILES: O=c1ccc(-c2ccc(NC3CCCCC3O)c(C(F)(F)F)c2)n[nH]1] | 354 | Method 1, 3 | <10 |
| YHHU-717 | 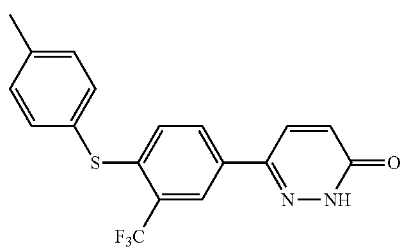 [SMILES: Cc1ccc(Sc2ccc(-c3ccc(=O)[nH]n3)cc2C(F)(F)F)cc1] | 363 | Method 3 | >1 |
| YHHU-718 | 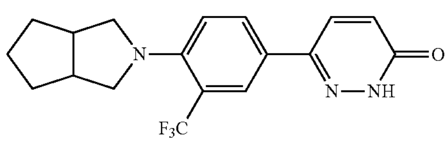 | 350 | Method 3 | <10 |

The above experimental results confirm that the novel pyridazinones of the present invention, which comprise 6-[3-(trifluoromethyl)phenyl]pyridazin-3(3H)-one as the mother nucleus and a electron-donating substitutents containing N, O, S or C at 4-position of aryl, have significant antitumor activities.

Example 16

The Effects of Compounds YHHU-744, YHHU-755, YHHU-756, YHHU-759 and YHHU-776 on Human Liver Cancer Cells Bel-7402 Transplanted Tumor on Nude Mice 1. Experimental Compounds Name and lot number: YHHU-744, a white powder, lot No.: No. c001471-106; YHHU-755, a white powder, lot No.: No. c001471-102; YHHU-756, a white powder, lot No.: No. c00147-106; YHHU-759, a white powder, lot No.: No. c001471-102; YHHU-776, a white powder, lot No.: No. c001471-107. Sorafenib was used as a positive control.

Formulation: YHHU-744, YHHU-755, YHHU-756, YHHU-759, YHHU-776 and the positive control were each diluted with 0.1% Tween-80 and distilled water to a desired concentration.

2. Laboratory Animal:

BALB/cA nude mice, 6-7 weeks old, ♀, were purchased from Shanghai SLAC Laboratory Animal Co. LTD. Certificate No.: SCXK (Shanghai) 2007-0005. Habitat: SPF level.

3. Experimental Procedure:

Human liver cancer cells Bel-7402 were inoculated on nude mice subcutaneously. After the tumor grew up to 300-450 mm$^3$, animals were grouped randomly (d0). Dosage and dosage regimen were shown in table 3. The tumor volume was measured 2-3 times each week and the weights of mice were recorded. The tumor volume was calculated according to as the following equation.

$V = \frac{1}{2} \times a \times b^2$ wherein, $a$ and $b$ are length and width, respectively.

4. Result:

Mice bearing cancer were consecutively administered with compounds YHHU-744, YHHU-755, YHHU-756, YHHU-759 or YHHU-776 intragastrically once a day for 11 days, and observation was continued to the 17$^{th}$ day. After administration, all tumors diminished significantly. At the 11$^{th}$ day, except for the group of compound YHHU-744 (4/5 vanished), all tumors vanished in the other groups (5/5), and no recrudescence was observed at the end of the experiment (results were shown in table 3 and FIG. 1). In addition, survivability of mice on all the above compounds was good, and no significant toxicity was observed.

Table 3 The therapeutic effect of compounds YHHU-744, YHHU-755, YHHU-756, YHHU-759, YHHU-776 and Sorafenib on human liver cancer cells Bel-7402 transplanted tumor on nude mice

| Drug | Dosage (mg/kg) | Administration | Tumor Volume (mm$^3$) | Inhibition Rate (%) | Quantity of Animals | Quantity of Animals Whose Tumors Vanished |
|---|---|---|---|---|---|---|
| solvent |  | PO, QD × 11 | 395.7 |  | 10 | 0 |
| Yhhu-744 | 100 | PO, QD × 11 | 343.7 | 98 | 5 | 4 |
| Yhhu-755 | 100 | PO, QD × 11 | 350.4 | 100 | 5 | 5 |
| Yhhu-756 | 100 | PO, QD × 11 | 294.6 | 100 | 5 | 5 |
| Yhhu-759 | 100 | PO, QD × 11 | 367.9 | 100 | 5 | 5 |
| Yhhu-776 | 100 | PO, QD × 11 | 338.2 | 100 | 5 | 5 |
| Sorafenib | 60 | PO, QD × 16 | 279.8 | 50 | 5 | 0 |

The invention claimed is:

1. A pyridazinone having the structure of formula I:

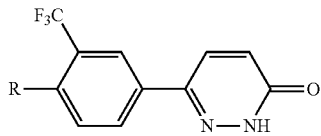

wherein,

R is —OH, —SH, substituted or unsubstituted $C_6$-$C_{12}$ aryl, substituted or unsubstituted heteroaryl, substituted or unsubstituted $C_3$-$C_{10}$ cyclic alkyl, substituted or unsubstituted heterocyclic group, —OR$_a$, —NHR$_a$, —NR$_a$R$_b$ or —SR$_a$, wherein R$_a$ and R$_b$ are independently selected from the group consisting of substituted or unsubstituted $C_1$-$C_{10}$ alkyl, substituted or unsubstituted $C_3$-$C_{10}$ cyclic alkyl, substituted or unsubstituted $C_6$-$C_{12}$ aryl, substituted or unsubstituted heteroaryl, and substituted or unsubstituted heterocyclic group;

the substituents are selected from the group consisting of halogen, —OH, —NO$_2$, $C_1$-$C_6$ alkyl, carboxyl, $C_1$-$C_6$ alkoxyl carbonyl, $C_6$-$C_{12}$ aryl, —NH$_2$, $C_1$-$C_6$ alkyl substituted amino, hydroxyl substituted $C_1$-$C_6$ alkyl, hydroxyl substituted $C_1$-$C_6$ alkoxyl group, unsubstituted or $C_1$-$C_6$ alkyl substituted heterocyclic group, and —CF$_3$;

the heteroaryl is 5- or 6-membered cyclic ring containing 1 to 3 heteroatoms selected from the group consisting of N, O and S;

the heterocyclic group is 3- to 7-membered monocyclic ring or 8-membered bicyclic ring which may contain 1 to 3 heteroatoms selected from the group consisting of N, O and S, and the heterocyclic group is optionally substituted with oxo group or sulfido group.

2. The pyridazinone according to claim 1, wherein,

R is —OH, —SH, substituted or unsubstituted phenyl, substituted or unsubstituted heteroaryl, substituted or unsubstituted $C_3$-$C_{10}$ cycloalkyl, substituted or unsubstituted heterocyclic group, —OR$_a$, —NHR$_a$, —NR$_a$R$_b$ or —SR$_a$, wherein, R$_a$ and R$_b$ are each independently substituted or unsubstituted $C_1$-$C_{10}$ alkyl, substituted or unsubstituted $C_3$-$C_{10}$ cycloalkyl, substituted or unsubstituted phenyl, substituted or unsubstituted heteroaryl, or substituted or unsubstituted heterocyclic group;

the substituents are selected from the group consisting of halogen, —OH, —NO$_2$, $C_1$-$C_6$ alkyl, carboxyl, $C_1$-$C_6$ alkoxylcarbonyl, phenyl, —NH$_2$, $C_1$-$C_6$ alkyl substituted amino, hydroxyl substituted $C_1$-$C_6$ alkyl, hydroxyl substituted $C_1$-$C_6$ alkoxyl, unsubstituted or $C_1$-$C_4$ alkyl substituted heterocyclic group and —CF$_3$;

the heteroaryl is 5- or 6-membered cyclic ring containing 1 to 3 nitrogen atoms;

the heterocyclic group is 3- to 7-membered monocyclic ring or 8-membered bicyclic ring, which may contain 1 to 3 nitrogen atoms, and the heterocyclic group is optionally substituted with oxo group or sulfido group.

3. A pyridazinone selected from the group consisting of:

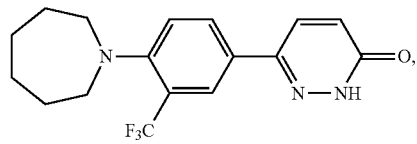

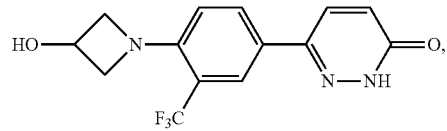

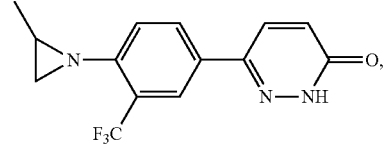

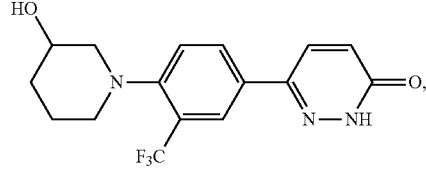

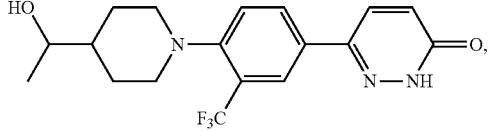

51
-continued
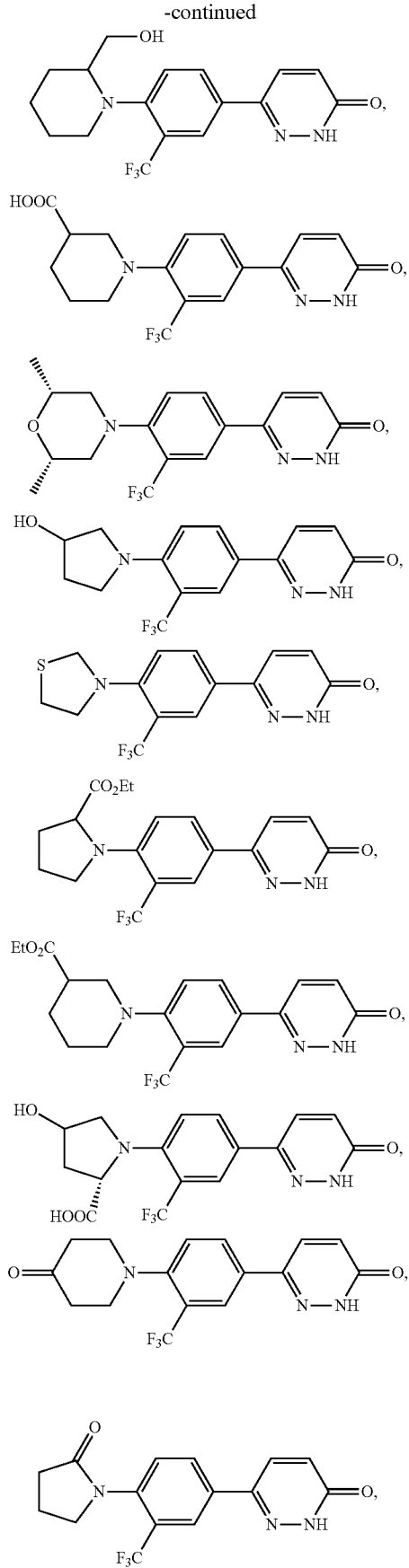
52
-continued
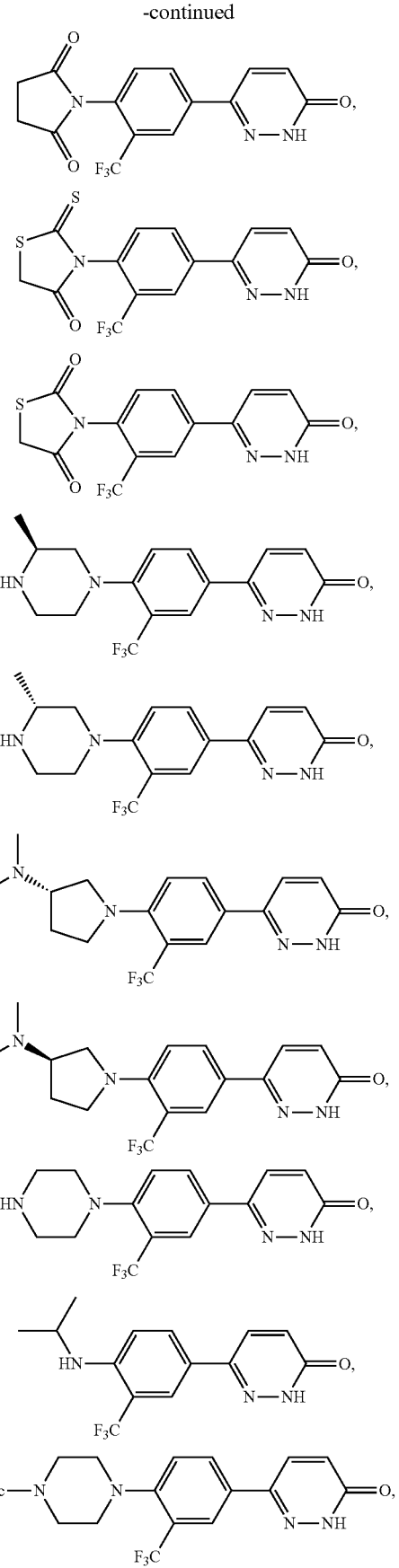

-continued
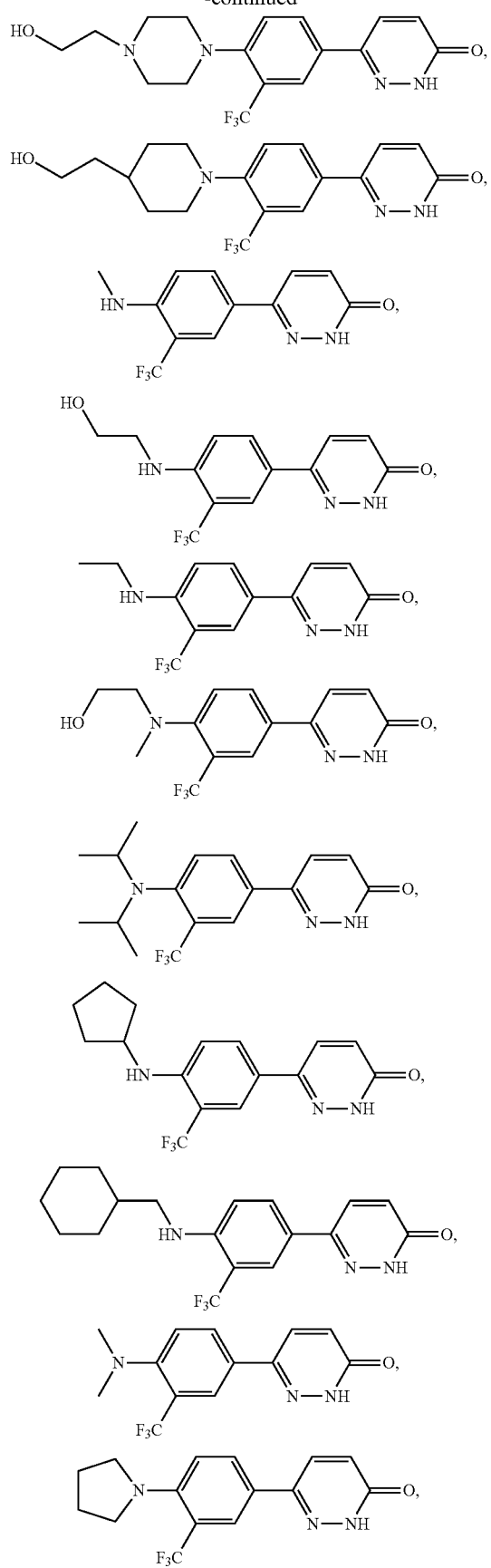
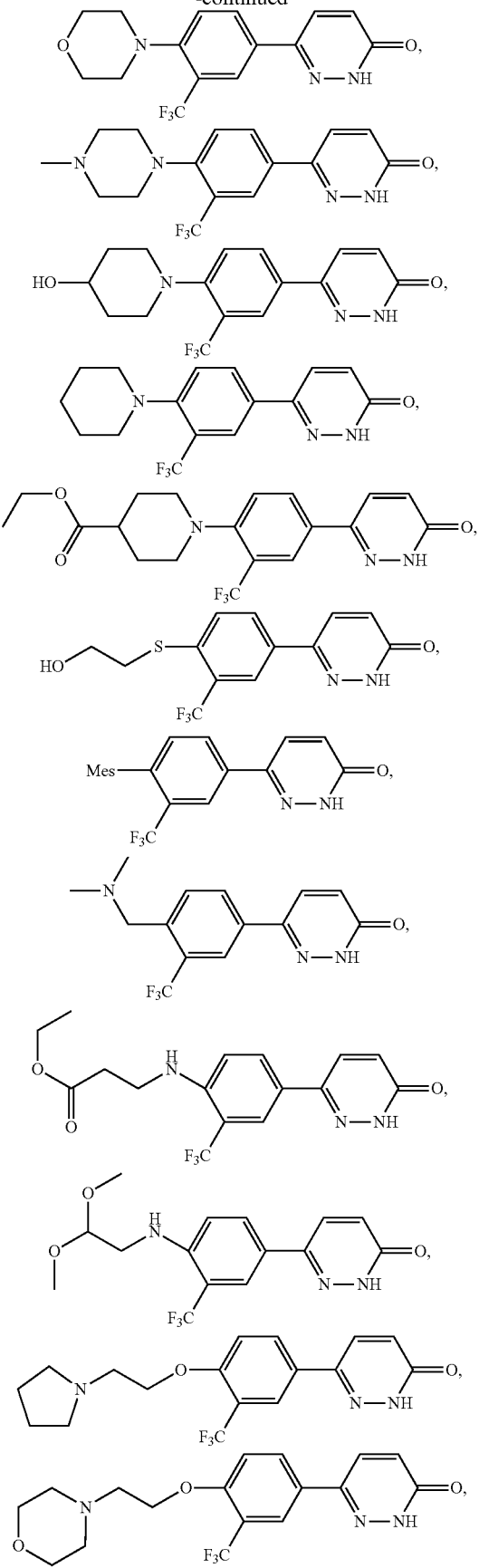

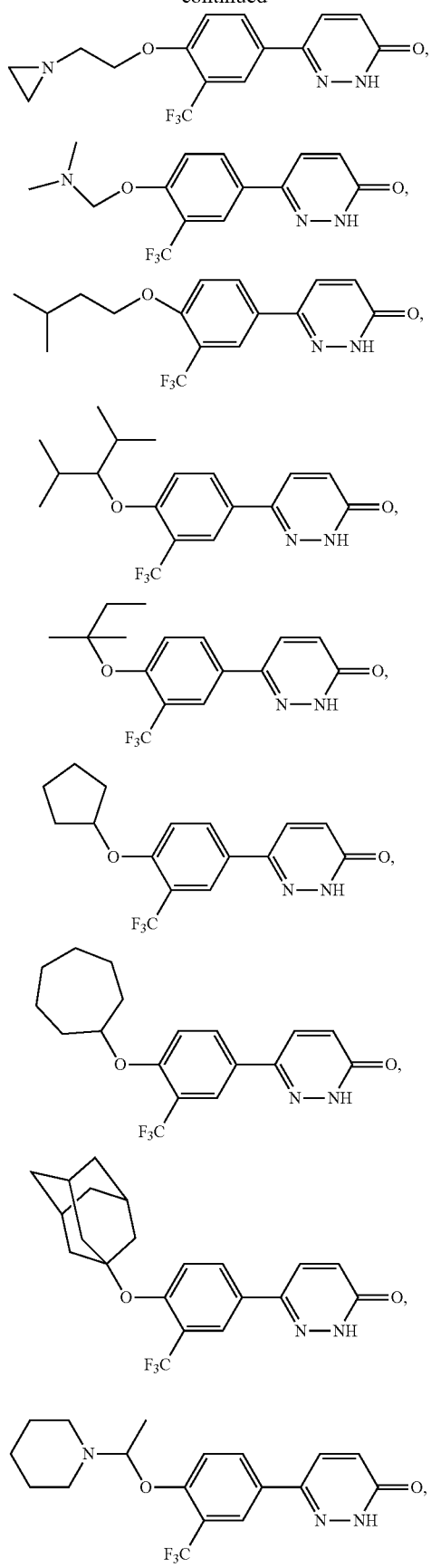
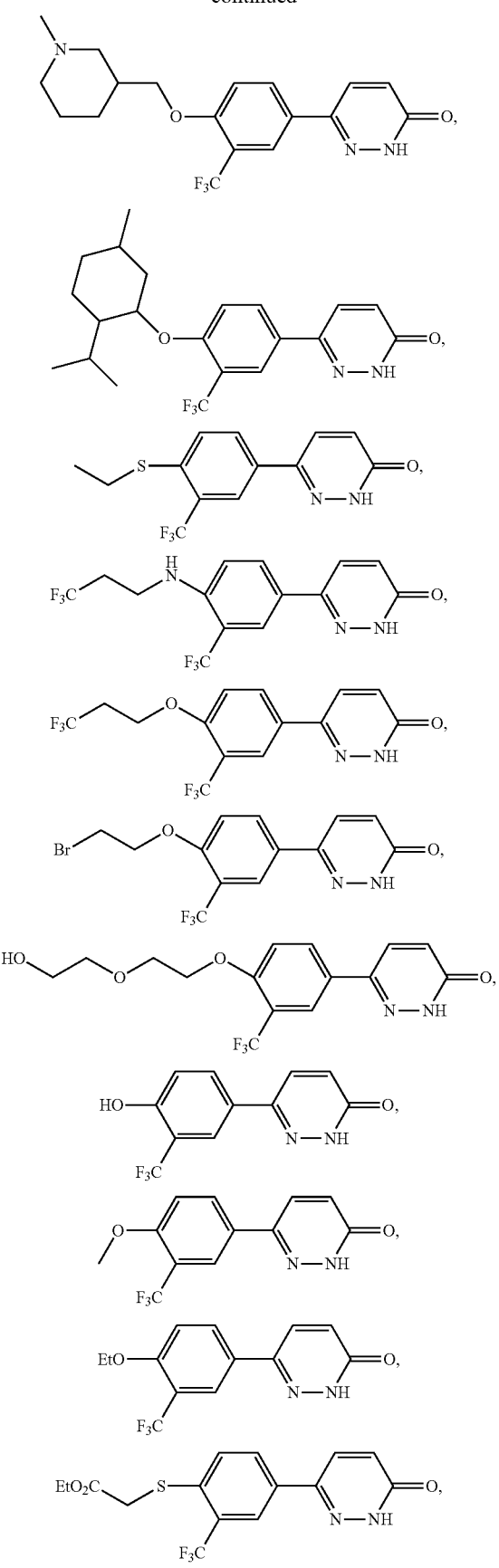

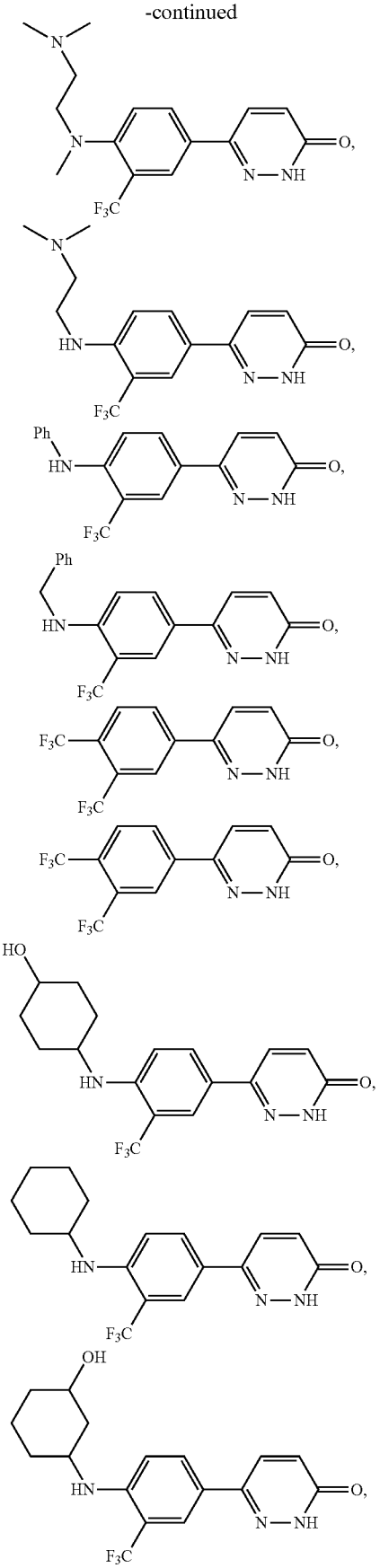

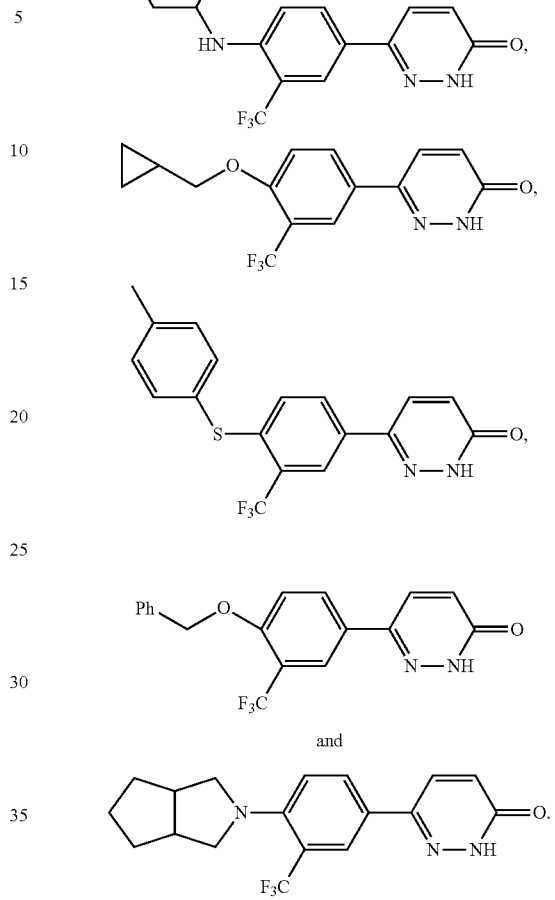

and

4. A pharmaceutical composition, comprising a therapeutically effective amount of the pyridazinone according to claim 1 and pharmaceutically acceptable adjuvants.

5. A pharmaceutical composition, comprising a therapeutically effective amount of the pyridazinone according to claim 2 and pharmaceutically acceptable adjuvants.

6. A pharmaceutical composition, comprising a therapeutically effective amount of the pyridazinone according to claim 3 and pharmaceutically acceptable adjuvants.

7. A method for preparing a pyridazinone of Formula I according to claim 1,

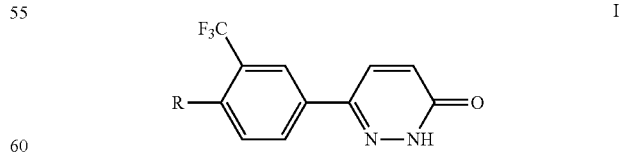

said method comprising:

a) reacting a m-trifluoromethylbenzaldehyde of formula 2, wherein R' is either R as defined as in claim 1 or a halogen atom, with methyl acrylate of formula 3 to produce a 1,4-dicarbonyl compound of formula 4;

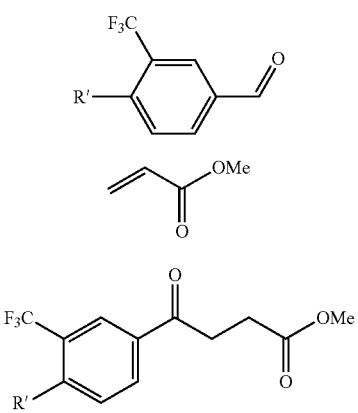

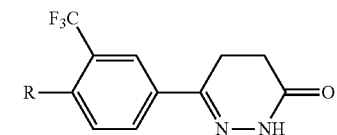

b) reacting the 1,4-dicarbonyl compound of formula 4 with a hydrazine hydrate to form a compound of formula 5;

[structure 5]

c) dehydrogenating the compound of formula 5 to produce the pyridazinone of Formula 1; and
d) if R' is a halogen atom, reacting the compound of formula 5 with a salt of an alcohol of formula $HOR_a$, an amine of formula $NH_2R_a$, or an amine of formula $HNR_aR_b$,
wherein $R_a$ and $R_b$ are defined as in claim 1.

8. The method for preparing a pyridazinone according to claim 7, wherein said reacting the 1,4-dicarbonyl compound of formula 4 comprises reacting the 1,4-dicarbonyl compound of formula 4 with hydrazine hydrate in ethanol under reflux.

9. The method for preparing a pyridazinone according to claim 7, wherein said dehydrogenating comprises dehydrogenating the compound of formula 5 with $CuCl_2.2H_2O$ to produce the pyridazinone of Formula 1.

10. A method for preparing a pyridazinone of Formula I according to claim 1, comprising:
a) reacting 3,6-dichloropyridazine of formula 7 with a phenylboronic acid of formula 6 to produce a 3-chloro-6-phenylpyridazine of formula 8; and

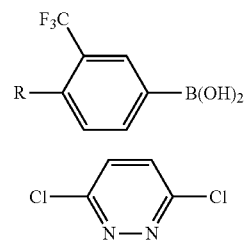

b) reacting the 3-chloro-6-phenylpyridazine of formula 8 with acetic acid to produce the pyridazinone of Formula I;
wherein R is defined as in claim 1.

11. The method for preparing a pyridazinone according to claim 10, wherein said reacting the phenylboronic acid comprises:
reacting the phenylboronic acid of formula 6 with 3,6-dichloropyridazine in the presence of a palladium catalyst to produce the 3-chloro-6-phenylpyridazine of formula 8.

* * * * *

UNITED STATES PATENT AND TRADEMARK OFFICE
CERTIFICATE OF CORRECTION

PATENT NO. : 8,501,731 B2
APPLICATION NO. : 12/933104
DATED : August 6, 2013
INVENTOR(S) : Youhong Hu et al.

It is certified that error appears in the above-identified patent and that said Letters Patent is hereby corrected as shown below:

In the Claims

In claim 3, column 57, lines 30-39, please delete the following structures:

" 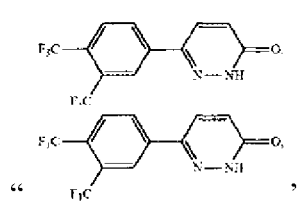 " and replace with -- 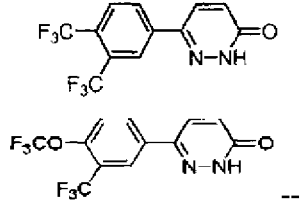 --

Signed and Sealed this
Seventeenth Day of September, 2013

Teresa Stanek Rea
*Deputy Director of the United States Patent and TrademarkOffice*